(12) United States Patent
Brizzi et al.

(10) Patent No.: US 8,476,408 B2
(45) Date of Patent: Jul. 2, 2013

(54) UNACYLATED GHRELIN AND ANALOGS AS THERAPEUTIC AGENTS FOR VASCULAR REMODELING IN DIABETIC PATIENTS AND TREATMENT OF CARDIOVASCULAR DISEASE

(75) Inventors: Maria Brizzi, Turin (IT); Giampiero Muccioli, Turin (IT); Ezio Ghigo, Turin (IT)

(73) Assignee: Alize Pharma SAS, Ecully (FR)

( * ) Notice: Subject to any disclaimer, the term of this patent is extended or adjusted under 35 U.S.C. 154(b) by 407 days.

(21) Appl. No.: 12/482,882

(22) Filed: Jun. 11, 2009

(65) Prior Publication Data

US 2010/0016226 A1 Jan. 21, 2010

Related U.S. Application Data

(60) Provisional application No. 61/061,163, filed on Jun. 13, 2008.

(51) Int. Cl.
*C07K 7/00* (2006.01)

(52) U.S. Cl.
USPC ............ 530/328; 530/326; 530/327; 530/329

(58) Field of Classification Search
USPC .................................. 530/326, 327, 328, 329
See application file for complete search history.

(56) References Cited

U.S. PATENT DOCUMENTS

| | | | | |
|---|---|---|---|---|
| 5,618,785 | A * | 4/1997 | Heavner et al. | 514/19.1 |
| 5,643,872 | A * | 7/1997 | Ali et al. | 424/94.64 |
| 5,695,761 | A * | 12/1997 | Denhardt et al. | 424/184.1 |
| 5,700,779 | A * | 12/1997 | Goodfellow et al. | 514/18.3 |
| 5,786,332 | A * | 7/1998 | Girten et al. | 514/7.6 |
| 5,840,691 | A * | 11/1998 | Furcht et al. | 514/9.3 |
| 5,932,548 | A * | 8/1999 | Deghenghi | 514/16.4 |
| 5,958,875 | A * | 9/1999 | Longo et al. | 514/8.4 |
| 6,627,729 | B1 | 9/2003 | Sheppard et al. | |
| 6,818,616 | B1 * | 11/2004 | Moyle et al. | 514/2.4 |
| 6,872,548 | B2 | 3/2005 | Coleman et al. | |
| 6,967,237 | B2 | 11/2005 | Bednarek | |
| 7,485,620 | B2 | 2/2009 | Ghigo et al. | |
| 7,666,833 | B2 | 2/2010 | Ghigo et al. | |
| 7,825,090 | B2 | 11/2010 | Ghigo et al. | |
| 2005/0175581 | A1* | 8/2005 | Haupts et al. | 424/85.1 |
| 2006/0293232 | A1* | 12/2006 | Levy et al. | 514/12 |
| 2007/0244047 | A1* | 10/2007 | Rosen et al. | 514/12 |
| 2008/0159991 | A1 | 7/2008 | Ghigo et al. | |
| 2008/0312133 | A1 | 12/2008 | Ghigo et al. | |

FOREIGN PATENT DOCUMENTS

| | | |
|---|---|---|
| CA | 2470235 A1 | 6/2003 |
| CA | 2471879 A1 | 11/2003 |
| CA | 2534507 A1 | 3/2005 |
| EP | 2067481 A1 | 6/2009 |
| WO | 0023469 * | 4/2000 |
| WO | 01/56592 A1 | 8/2001 |
| WO | 01/87335 A2 | 11/2001 |
| WO | 01/92292 A2 | 12/2001 |
| WO | 02/060472 A1 | 8/2002 |
| WO | 03/051389 A2 | 6/2003 |
| WO | WO 2005/039624 A1 | 5/2005 |
| WO | 2006/045319 A2 | 5/2006 |
| WO | WO 2007/126792 A1 | 11/2007 |
| WO | 2008/145749 A1 | 12/2008 |
| WO | 2009/071283 A2 | 6/2009 |

OTHER PUBLICATIONS

Leifheit-Nestler Maren (Arteriosclerosis, Thrombosis, and Vascular Biology 30(7), 1398-1406, 2010).*
Cheng Susan, Atherosclerosis, (Jan. 2012) vol. 220, No. 1, pp. 145-150.*
Asahara Takayuki, et al. "Isolation of putative progenitor endothelial cells for angiogenesis," Science, 1997, 275:964-7 (Abstract only).
Asahara, Takayuki et al., "Vasculogenesis in Physiological and Pathological Neovascularization Bone Marrow Origin of Endothelial Progenitor Cells Responsible for Postnatal," Circulation Research, 1999, 85:221-228.
Assmus, Birgit, et al., "Transplantation of Progenitor Cells and Regeneration Enhancement in Acute Myocardial Infarction (TOPCARE—AMI)," Circulation, 2002, 106:3009-3017.
Fadini, Gian Paolo, et al., "Gender Differences in Endothelial Progenitor Cells and Cardiovascular Risk Profile : The Role of Female Estrogens," Arterioscler Thromb Vasc Biol, 2008, 28:997-1004.
Hiasa, Ken-ichi, et al., "Gene Transfer of Stromal Cell-Derived Factor-1α Enhances Ischemic Vasculogenesis and Angiogenesis via Vascular Endothelial Growth Factor/Endothelial Nitric Oxide Synthase-Related Pathway : Next-Generation Chemokine Therapy for Therapeutic Neovascularization," Circulation, 2004, 109:2454-2461.
Huang, Pingping, et al., "Autologous Transplantation of Granulocyte Colony—Stimulating Factor—Mobilized Peripheral Blood Mononuclear Cells Improves Critical Limb Ischemia in Diabetes," Diabetes Care, 2005, 28:2155-2160.
Kamihata, Hiroshi, et al., "Improvement of Collateral Perfusion and Regional Function by Implantation of Peripheral Blood Mononuclear Cells Into Ischemic Hibernating Myocardium," Arterioscler Thromb Vasc Biol, 2002, 22:1804-1810.
Murohara, Toyoaki, et al., "Transplanted cord blood-derived endothelial precursor cells augment postnatal neovascularization," The Journal of Clinical Investigation, 2000, 105:1527-1536.

(Continued)

*Primary Examiner* — David Lukton
(74) *Attorney, Agent, or Firm* — Fish & Richardson P.C.

(57) ABSTRACT

The present invention relates to a method for treating a cardiovascular disease, for increasing the number of circulating angiogenic cells (CAC) and/or improving the function of CAC and a method for improving vascular remodeling and/or neovascularisation. The method comprises administering to the subject a therapeutically effective amount of unacylated ghrelin or a polypeptide comprising the amino acid sequence set forth in SEQ ID NO: 1 or a fragment or analog thereof having the biological activity of SEQ ID NO: 1; and to pharmaceutical compositions comprising unacylated ghrelin or a polypeptide comprising the amino acid sequence set forth in SEQ ID NO: 1 or a fragment or analog thereof having the biological activity of SEQ ID NO: 1.

13 Claims, 23 Drawing Sheets

OTHER PUBLICATIONS

Tateishi-Yuyama, Eriko, et al., "Therapeutic angiogenesis for patients with limb ischaemia by autologous transplantation of bone-marrow cells: a pilot study and a randomised controlled trial," The Lancet, 2002, 360:427-435 (Astract only).

Togliatto, Gabriele, et al., "Unacylated Ghrelin Rescues Endothelial Progenitor Cell Function in Individuals With Type 2 Diabetes." Diabetes, 2010, 59:1016-1025.

Urbich, Carmen, et al., "Endothelial Progenitor Cells: Characterization and Role in Vascular Biology," Circulation Research, 2004, 95:343-353.

Werner, Nikos, et al., "Circulating Endothelial Progenitor Cells and Cardiovascular Outcomes," The New England Journal of Medicine, 2005, 353:999-1007.

Office Action mailed on Apr. 29, 2010 in connection with U.S. Appl. No. 12/130,615.

Salehi et al., Effects of ghrelin on insulin and glucagon secretion: a study of isolated pancreatic islets and intact mice, Regulatory Peptides 118 (2004) 143-150.

Official Communication issued on Jun. 1, 2011 in connection with European Patent Application No. 09 761 776, 4 pages.

Office Action issued by USPTO on Jun. 9, 2011 in connection with U.S. Appl. No. 12/130,615, 11 pages.

Wells, James A., Additivity of Mutational Effects in Proteins, Biochemistry, vol. 29, No. 27, Sep. 18, 1990, pp. 8509-8517.

Kojima M, Hosoda H, Date Y, Nakazato M, Matsuo H and Kangawa K; Ghrelin is a growth-hormone-releasing acylated peptide from stomach, Nature 402:656-660 (1999).

Gnanapavan S, Kola B, Bustin SA, Morris DG, McGee P, Fairclough P, Bhattacharya S, Carpenter R, Grossman AB and Korbonits M; The tissue distribution of the mRNA of ghrelin and subtypes of its receptor. GHS-R, in humans, J. Clin. Endocrinol. Metab. 87:2988-2991 (2002).

Howard AD, Feighner SD, Cully DF, Arena JP, Liberator PL, Rosenblum CI, Hamelin M, Hreniuk DL, Palyha OC, Anderson J, Paress PS, Diaz C, Chou M, Liu KK, McKee K-K, Pong S-S, Chaung L-Y, Elbrecht A, Dashkevicz M, Heavens R, Rigby M. Sirinathsinghji D, Dean DC, Melillo DG, Patchett AA, Nargund R. Griffin PR, DeMartino JA, Gupta SK, Schaeffer JA, Smith RG, Van der Ploeg LHT; A receptor in pituitary and hypothalamus that functions in growth hormone release. Science 273:974-977 (1996).

Li A, Cheng G, Zhu GH, Tarnawski AS; Ghrelin stimulates angiogenesis in human microvascular endothelial cells : Implications beyond GH release. Biochem. Byophis. Res. commun. 353:238-43 (2007).

Li WG, Gavrila D, Liu X, Wang L, Gunnlaugsson S, Stoll LL, McCormick ML, Sigmund CD, Tang C, Weintraub NL; Ghrelin inhibits proinflammatoty response and nuclear factor-kappa B activation in human endothelial cells. Circulation 109:2221-6 (2004).

Dixit VD, Schaffer EM, Pyle RS, Collins GD, Sakthivel SK, Palaniappan R, Lillard JW Jr, Taub DD; Ghrelin inhibits leptin-and activation-induced proinflammatory cytokines expression by human monocytes and T cells. J. Clin. Inv. 114:57-66 (2004).

van der Lely AJ, Tschop M, Heiman ML, Ghigo E; Biological, physiological, pathophysiological, and pharmacological aspects of ghrelin. Endocr Rev 25:426-457 (2004).

Baldanzi G, Filigheddu N, Cutrupi S, Catapano F, Bonissoni S, Fubini A, Malan D, Baj G, Granata R, Broglio F, Papotti M, Surico N, Bussolino F, Isgaard J, Deghenghi R, Sinigaglia F, Prat M, Muccioli G, Ghigo E, Graziani A; Ghrelin and des-acyl ghrelin inhibit cell death in cardiomyocytes and endothelial cells through ERK1/2 and PI 3-kinase/AKT. J Cell Biol. 159:1029-37 (2002).

Delhanty PJ, van der Eerden BC, van der Velde M, Gauna C, Pols HA, Jahr H, Chiba H, van der Lely AJ, van Leeuwen J; Ghrelin and unacylated ghrelin stimulate human osteoblast growth via mitogen-activated protein kinase (MAPK)/phosphoinositide 3-kinase (PI3K) pathways in the absence of GHS-R1a, J Endocrinol. 188:37-47 (2006).

Choi K, Roh SG, Hong YH, Shrestha YB, Hishikawa D, Chen C. Kojima M, Kangawa K, Sasaki S; The role of ghrelin and growth hormone secretagogues receptor on rat adipogenesis. Endocrinology. 144:754-9 (2003).

Sorrentino SA, Bahlmann FH, Besler C, Mueller M, Schulz S, Kirchhoff N, Doerries C, Horvath T, Limbourg A, Limbourg F, Fliser D, Haller H, Drexler H, Landmesser U; Oxidant stress impairs in vivo reendothelialization capacity of endothelial progenitor cells from patients with type 2 diabetes mellitus: restoration by the peroxisome proliferator-activated receptor-gamma agonist rosiglitazone. Circulation 116:163-73 (2007).

Brizzi MF, Dentelli P, Pavan M, Rosso A, Gambino R, Grazia De Cesaris M, Garbarino G, Camussi G, Pagano G, Pegoraro L; Diabetic LDL inhibits cell-cycle progression via STAT5B and p21(waf). J Clin Invest. 109:111-9 (2002).

Thum T, Fraccarollo D, Schultheiss M, Froese S, Galuppo P, Widder JD, Tsikas D, Ertl G, Bauersachs J; Endothelial nitric oxide synthase uncoupling impairs endothelial progenitor cell mobilization and function in diabetes. Diabetes 56:666-74 (2007).

Dimmeler S, Zeiher AM; Vascular repair by circulating endothelial progenitor cells: the missing link in atherosclerosis? J Mol Med. 82:671-7 (2004).

Tepper OM, Galiano RD, Capla JM, Kalka C, Gagne PJ, Jacobowitz GR, Levine JP, Gurtner GC; Human endothelial progenitor cells from type II diabetics exhibit impaired proliferation, adhesion, and incorporation into vascular structures. Circulation 106:2781-6 (2002).

Papayannopoulou T; Current mechanistic scenarios in hematopoietic stem/progenitor cell mobilization. Blood 103:1580-5 (2004).

Hattori K, Heissig B, Tashiro K, Honjo T, Tateno M, Shieh JH, Hackett NR, Quitoriano MS, Crystal RG, Rafii S, Moore MA; Plasma elevation of stromal cell-derived factor-1 induces mobilization of mature and immature hematopoietic progenitor and stem cells. Blood 97:3354-60 (2001).

Takahashi T, Kalka C, Masuda H, Chen D. Silver M, Kearney M, Magner M, Isner JM, Asahara T; Ischemia- and cytokine-induced mobilization of bone marrow-derived endothelial progenitor cells for neovascularization. Nat Med. 5:434-8 (1999).

Hill JM, Zalos G, Halcox JP, Schenke WH, Waclawiw MA, Quyyumi AA, Finkel T: Circulating endothelial progenitor cells, vascular function, and cardiovascular risk. N Engl J Med. 348:593-600 (2003).

Defilippi P. Rosso A, Dentelli P, Calvi C, Garbanno G, Tarone G, Pegoraro L, Brizzi; MFb1 Integrin and IL-3R coordinately regulate STAT5 activation and anchorage-dependent proliferation, J. Cell Biol. 168:1099-1108 (2005).

Zhao W, Diz DI, Robbins ME; Oxidatve damage pathways in relation to normal tissue injury. Br J Radiol. 80:S23-31 (2007).

Rosso A, Balsamo A, Gambino R, Dentelli P, Falcioni R. Cassader M. Pegoraro L, Pagano G, Brizzi MF; p53 Mediates the accelerated onset of senescence of endothelial progenitor cells in diabetes. J Biol Chem. 281:4339-47 (2006).

Brummelkamp, TR., Bernards, R and Agami, R; A system for stable expression of short interfering RNAs in mammalian cells. Science 296:550-553 (2002).

Dentelli P, Rosso A, Balsamo A, Colmenares Benedetto S, Zeoli A, Pegoraro M, Camussi G, Pegoraro L, Brizzi MF; C-KIT, by interacting with the membrane-bound ligand, recruits endothelial progenitor cells to inflamed endothelium. Blood. 109:4264-71 (2007).

Aranguren XL, Luttun A, Clavel C, et al.; In vitro and in vivo arterial differentiation of human multipotent adult progenitor cells. Blood. 109:2634-2642 (2007).

Cormier S, Vandormael-Pournin S, Babinet C, Cohen-Tannoudji M; Developmental expression of the Notch signaling pathway genes during mouse preimplantation development. Gene Expr. Patterns.;4:713-717 (2004).

Hoff J; Methods of blood collection in the mouse. Lab. Animal 29 (2000), pp. 47-53.

Zeoli A, Dentelli P, Rosso A, Togliatto G, Trombetta A, Damiano L, Francia di Celle P, Pegoraro L, Altruda F, Brizzi MF; Interleukin-3 (IL-3) promotes expansion of hemopoietic-derived CD45+ angiogenic cells and their arterial commitment via STAT5 activation. Blood in press. Jul. 15, 2008, vol. 112, No. 2, pp. 350-361.

Yamagishi S, Matsui T, Nakamura K; Kinetics, role and therapeutic implications of endogenous soluble form of receptor for advanced glycation end products (sRAGE) in diabetes, Curr Drug Targets, 8:1138-43(2007).

Dimri GP. What has senescence got to do with cancer? Cancer Cell, 7:505-12 (2005), pp. 1-16.

Vasa M. Fichtlscherer S. Aicher A, Adler K, Urbich C, Martin H, Zeiher AM, Dimmeler S. Number and migratory activity of circulating endothelial progenitor cells inversely correlate with risk factors for coronary artery disease. Circ Res. 89: E1-7 (2001).

Waltenberger J. Impaired collateral vessel development in diabetes: potential cellular mechanisms and therapeutic implications. Cardiovasc Res 49:554-60 (2001).

Abaci A, Oguzhan A, Kahraman S, Eryol NK, Unal S, Arinc H, Ergin A. Effect of diabetes mellitus on formation of coronary collateral vessels. Circulation 99:2239-42 (1999).

Schalkwijk CG, Stehouwer CD. Vascular complications in diabetes mellitus: the role of endothelial dysfunction. Clin Sci (Lond) 109:143-59 (2005).

Kleinz MJ, Maguire JJ, Skepper JN, Davenport AP. Functional and immunocytochemical evidence for a role of ghrelin and des-octanoyl ghrelin in the regulation of vascular tome in man. Cardiovascular Research 69:227-235 (2006).

Adelhorst, et al, "Structure-Activity Studies of Glucagon-like Peptide-1", The Journal of Biological Chemistry, vol. 269, No. 9, Mar. 4, 1994, pp. 6275-6278.

Broglio,et al., "Non-Acylated Ghrelin Counteracts the Metabolic but not the Neuroendocrine Response to Acylated Ghrelin in Humans" The J. of clinical Endocrinology and Metabolism, 2001, Vol. 86, pp. 1738-1745.

Cassoni, et al. "Identification, Charaterization, and Biological Activityof Specific Receiptors for Natural (Ghrelin) and Synethic Growth Secretagoguesn and Analogues in Human Breast Carcinoma and Cell Lines," The Journal of Clinical Endocrinology & Metabolism, 2001, vol. 86, pp. 1738-1745.

Granata, et al., Acylated and unacylated ghrelin promote proliferation and inbit serum starvation and cytokine induced apoptosis pf pancea b cells through cAMP/PKA, ERK1/2 and PL3K/Akt, abstract and poster from Endocrine Society Meeting, Boston, Jun. 24-27, 2006.

Granata, et al."Acylated and unacylated ghren promote proliferation and inhibit apoptosis of Pancreatic b cells and Human Islets. Involvement of 3', 5'—Cyclic Adenosine Monophosphate/Protein Kinase A, Extracellualar Signal-Regulated Kinase 1/2 and Phesphatidyl Inusitol 3-Kinase/Akt Signaling", Endocrinolgy, Feb. 2007, 148 (2), pp. 512-529.

Marzullo, et al., "The Relationship between Active Ghrelin and Human Obesity. involves Alteration in Resting Energy Expenditure" The Journal of Clinical Endecrinolgy and Metabolism 89(2), 2004, pp. 936-939.

Mickle, et al"Genotype-Phenotype Relationship in Cystic Fibrosis Inherited Diseases of the Pancreas", vol. 84 No. 3, May 2000, pp. 597-607.

Poykko, et al"Low Plasma Ghrelin is Associated with Insulin Resitance, Hypertension, and the Prevalence of Type 2 Diabetes" Diabetes, vol. 52, Oct. 2003, pp. 2546-2553.

Prodam, et al."Unacylated ghrelin (UAG) ehnances the early insuling responses to meak improves glucose metabolism and decrease free fatty acids levels in helathy volunteers"abstract and poster from EP Congress of Endocrinology, Budapest, Apr. 28-May 2, 2007.

Soares, et al "Ghrelin, des-acyl ghrelin and obestatin: Three pieces of the same puzzle", Elesvier, Peptides 29 (2008), Mar. 4, 2008, pp. 1255-1270.

Atkinson, et al"Type 1 diabetes: new perspectives on diease pathogenesis and treatment". The Lancet. vol. 358, Jul. 21, 2001, pp. 221-229.

Florez, et al."The Genetics of Type 2 Diabetes: a Realistc Appraisal in 2008" Journalof Clinical Endocrinoliogy Metabolism, Dec. 2008, 93 (12), pp. 4633-4642.

Toshinai, et al"Upregulation of Ghrelin Expression in the Stomach upon upon Fasting Insulin-induced Hypoglycemia and ceptin administration" Biochemical and Biophysical Research. Committee. 281, Feb. 6, 2001, pp. 1220-1225.

Li et al., Cardioprotective effects of ghrelin and des-ghrelin on myocardial injury induced by isoproterenol in rats, Acta Pharmacologia Sinica, 27:527-535 (2006).

Office Action issued on Oct. 1, 2010 in connection with U.S. Appl. No. 12/130,615, 8 pp.

Office Action issued on Oct. 16, 2009 in connection with U.S. Appl. No. 12/130,615, 18 pp.

International Search Report mailed on Jan. 25, 2010 in connection with International Patent Application PCT/EP2009/057263 (WO 2009/150214 A3).

Final Office Action mailed on Feb. 16, 2011 in connection with U.S. Appl. No. 12/130,615.

Office Action mailed Feb. 26, 2013, which issued in U.S. Appl. No. 12/600,407.

PubMed Health Encyclopedia (dyslipidemia); http://www.ncbi.nlm.nih.gov/pubmedhealth/PMH0002194 (2012).

PubMed Health Encyclopedia (diabetes); http://www.ncbi.nlm.nih.gov/pubmedhealth/PMH0002194 (2012).

PubMed Health Encyclopedia (obesity); http://www.ncbi.nlm.nih.gov/pubmedhealth/PMH0002194 (2012).

* cited by examiner

SEQUENCE LISTING

```
<160> NUMBER OF SEQ ID NOS: 12

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 14
<212> TYPE: PRT
<213> ORGANISM: Homo sapiens

<400> SEQUENCE: 2

Gly Ser Ser Phe Leu Ser Pro Glu His Gln Arg Val Gln Gln
1               5                   10

<210> SEQ ID NO 3
<211> LENGTH: 18
<212> TYPE: PRT
<213> ORGANISM: Homo sapiens

<400> SEQUENCE: 3

Gly Ser Ser Phe Leu Ser Pro Glu His Gln Arg Val Gln Gln Arg Lys
1               5                   10                  15

Glu Ser

<210> SEQ ID NO 4
<211> LENGTH: 5
<212> TYPE: PRT
<213> ORGANISM: Homo sapiens

<400> SEQUENCE: 4

Gly Ser Ser Phe Leu
1               5

<210> SEQ ID NO 5
<211> LENGTH: 12
<212> TYPE: PRT
<213> ORGANISM: Homo sapiens
```

```
<400> SEQUENCE: 5

Glu Ser Lys Lys Pro Pro Ala Lys Leu Gln Pro Arg
1               5                   10

<210> SEQ ID NO 6
<211> LENGTH: 8
<212> TYPE: PRT
<213> ORGANISM: Homo sapiens

<400> SEQUENCE: 6

Ser Pro Glu His Gln Arg Val Gln
1               5

<210> SEQ ID NO 7
<211> LENGTH: 6
<212> TYPE: PRT
<213> ORGANISM: Homo sapiens

<400> SEQUENCE: 7

Glu His Gln Arg Val Gln
1               5

<210> SEQ ID NO 8
<211> LENGTH: 5
<212> TYPE: PRT
<213> ORGANISM: Homo sapiens

<400> SEQUENCE: 8

Glu His Gln Arg Val
1               5

<210> SEQ ID NO 9
<211> LENGTH: 4
<212> TYPE: PRT
<213> ORGANISM: Homo sapiens

<400> SEQUENCE: 9

His Gln Arg Val
1

<210> SEQ ID NO 10
<211> LENGTH: 3
<212> TYPE: PRT
<213> ORGANISM: Artificial sequence
<220> FEATURE:
<223> OTHER INFORMATION: Synthetic peptide

<400> SEQUENCE: 10

His Gln Arg
1

<210> SEQ ID NO 11
<211> LENGTH: 14
<212> TYPE: PRT
<213> ORGANISM: Artificial sequence
<220> FEATURE:
<223> OTHER INFORMATION: Synthetic peptide

<400> SEQUENCE: 11

Gln Gln Val Arg Gln His Glu Pro Ser Leu Phe Ser Ser Gly
1               5                   10

<210> SEQ ID NO 12
<211> LENGTH: 4
<212> TYPE: PRT
```

```
<213> ORGANISM: Homo sapiens

<400> SEQUENCE: 12

Glu His Gln Arg
1
```

UNACYLATED GHRELIN AND ANALOGS AS THERAPEUTIC AGENTS FOR VASCULAR REMODELING IN DIABETIC PATIENTS AND TREATMENT OF CARDIOVASCULAR DISEASE

CROSS-REFERENCE TO RELATED APPLICATIONS

This application claims the benefit of and priority to U.S. provisional application No. 61/061,163 filed Jun. 13, 2008, the content of which is herein incorporated by reference.

REFERENCE TO SEQUENCE LISTING

Pursuant to 37 C.F.R. 1.821(c), a sequence listing is submitted electronically herewith via EFS Web as an ASCII compliant text file named "Sequence Listing.txt" that was created on Oct. 21, 2011, and has a size of 2306 bytes. The content of the aforementioned file named "Sequence Listing.txt" is hereby incorporated by reference in its entirety.

FIELD OF THE INVENTION

This invention relates to vascular remodeling and to the treatment of vascular diseases, to methods and pharmaceutical compositions for treating a cardiovascular disease, methods and pharmaceutical compositions for increasing the number of circulating angiogenic cells (CAC) and/or improving the function of CAC, and methods and pharmaceutical compositions for improving vascular remodelling and/or neovascularisation.

BACKGROUND ART

Ghrelin (AG) is a 28 amino acid peptide, purified and identified from rat stomach, and characterized by the presence of an n-octanoyl modification on the $Ser^3$ residue (Ref. 1). AG is the endogenous ligand of the growth hormone secretagogue receptor (GHSR) (Refs. 2, 3) and in addition to growth-hormone-releasing properties, AG is also detected in the cardiovascular system including in the heart, vasculature and endothelial cells of large vessels, indicating that it may also influence vascular biology, vascular physiology, and atherogenesis (Refs. 4, 5, 6).

Des-acyl ghrelin (or unacylated ghrelin, UAG), the unacylated form of ghrelin, whose concentration in plasma and tissue is higher, compared to AG, fails to bind GHSR-1a and is devoid of any central activity (Ref. 7). However, UAG shares with AG many biological activities and common binding sites on several peripheral tissues. AG and UAG exhibit similar GHS-R independent biological activities, including a cytoprotective effect (Ref. 9) and an effect on adipogenesis in vivo (Ref. 10). In most, but not all, of the cells where UAG activity was evaluated, GHSR-1a is not expressed, suggesting that such pleiotropic activities shared with AG may be mediated by a yet unidentified receptor distinct from GHSR-1a.

It has been demonstrated that UAG is a biologically active peptide, particularly at the metabolic level, having notably been shown to exert anti-diabetogenic effects as described in U.S. Pat. No. 7,485,620, in U.S. patent application publication number U.S. 20080159991, in U.S. patent application publication number U.S. 20080312133 and in WO/2008/145749.

It was previously generally reported that AG and UAG act directly on cardiomyocytes to inhibit experimentally-induced cell death through activation of a survival signaling pathway (Ref. 8). AG was also shown to inhibit basal and TNF-α-induced chemotactic cytokine production and mononuclear cell adhesion in human umbilical vein endothelial cells (HUVECs) (Ref. 5). It was further reported that treatment of human microvascular endothelial cells (HMVECs) with exogenous AG significantly increased cell proliferation, migration, in vitro angiogenesis and ERK2 phosphorylation in these cells (Ref. 4). Recently, Kleinz et al. (Ref. 35) demonstrated that AG and UAG play a role in the paracrine regulation of vascular tone in humans; more specifically they showed that AG and UAG have vasodilator actions in human arteries.

Accelerated vascular disease is the major cause of death and disability in patients with diabetes. Endothelial injury is thought to represent a crucial step in initiation and progression of atherosclerotic vascular disease in diabetes setting (Ref. 11).

It was previously reported that advanced glycated end products (AGEs) contribute to impaired vascular remodeling in the diabetic setting (Ref. 12). The formation of AGEs and the production of reactive oxygen species (ROS), as a cellular response to AGE in diabetes, seem to mainly contribute to these events.

Vascular remodeling does not rely exclusively on proliferation of resident endothelial cells but also involves circulating endothelial progenitor cells (EPC). Recent data demonstrated that in patients with cardiovascular risk factors such as, but not limited to, patients with diabetes, the number of EPC is reduced and their function impaired (Refs. 13, 14, 15).

Two types of EPC have so far been described, the early and late EPC. Although they share common features, they have some distinct features with respect to morphology, proliferative potential, and in vitro functional characteristics. Unlike late EPC, early EPC do not adopt a typical endothelial phenotype in vitro but enhance neovascularization in an indirect paracrine fashion in vivo. This led to redefining these cells as circulating angiogenic cells (CAC). CAC, that are monocyte-like cells, may home from the bone-marrow into sites of neovascularization, participate in re-endothelization after vascular injury and differentiate into mature endothelial cells in situ (Ref. 16).

Compelling evidence indicates that as the cardiovascular risk factor profile increases, CAC number decreases and CAC functional activity is impaired, thus limiting CAC delivery to, for example, sites of ischemia where angiogenesis could be required. Treatment with certain cytokines induces bone-marrow (BM) mobilization of CAC which, in turn, likely protects against cardiovascular risk (Refs. 17, 18).

Oxidative stress plays a major role in vascular tissue damage and endothelial injury associated with diabetes. Mainly, the production of ROS in this setting is induced by advanced glycated end products (AGEs), notably produced from CAC.

There is an important need to design a way to improve vascular remodeling and noevascularization in patients at risk of suffering from a cardiovascular disease or suffering from a cardiovascular disease in order to prevent or to treat cardiovascular diseases. One solution is to increase CAC cell number and/or improve CAC functionality, which can be achieved by, improving their mobilization from the bone marrow, decreasing ROS production induced by AGEs, decreasing CAC senescence or apoptosis rate, and by enhancing CAC capacity to differentiate into an arterial or a venous phenotype (i.e., to form vessels in vivo).

The earlier observations that AG may have an effect on vascular dysfunction and cardio-protection led to evaluate the in vitro and in vivo effect of UAG on same, as well as to evaluate the effect of UAG on CAC biology, which notably, has not been demonstrated before.

SUMMARY OF THE INVENTION

According to one aspect, the present invention relates to a method for treating a cardiovascular disease in a subject, comprising administering to the subject a therapeutically effective amount of a polypeptide comprising the amino acid sequence set forth in SEQ ID NO: 1 or a fragment or analog thereof having the biological activity of SEQ ID NO: 1.

According to another aspect, the present invention relates to a method for increasing the number of circulating angiogenic cells (CAC) and/or improving the function of CAC in a subject, comprising administering to the subject a therapeutically effective amount of a polypeptide comprising the amino acid sequence set forth in SEQ ID NO: 1, or a fragment or analog thereof having the biological activity of SEQ ID NO: 1.

According to another aspect, the present invention relates to a method for improving vascular remodeling and/or neovascularization in a subject comprising administering to the subject a therapeutically effective amount of a polypeptide comprising the sequence set forth in SEQ ID NO: 1, or a fragment or analog thereof having the biological activity of SEQ ID NO: 1.

According to another aspect, the present invention relates to a pharmaceutical composition for use in the treatment of a cardiovascular disease, comprising a therapeutically effective amount of a polypeptide, wherein the polypeptide comprises the amino acid sequence set forth in SEQ ID NO: 1, or a fragment or analog thereof having the biological activity of SEQ ID NO: 1, together with a pharmaceutically acceptable carrier.

According to another aspect, the present invention relates to an isolated polypeptide comprising the amino acid sequence set forth in SEQ ID NO: 1, or a fragment or analog thereof having the biological activity of SEQ ID NO: 1, for increasing the number of circulating angiogenic cells (CAC) and/or improving the function of CAC in a subject.

According to another aspect, the present invention relates to an isolated polypeptide comprising the amino acid sequence set forth in SEQ ID NO: 1, or a fragment or analog thereof, for improving vascular remodeling and/or neovascularization in a subject.

According to another aspect, the present invention relates to an isolated polypeptide comprising the amino acid sequence set forth in SEQ ID NO: 1, or a fragment or analog thereof, for improving wound healing in a subject.

According to another aspect, the present invention relates to an isolated polypeptide comprising the amino acid sequence set forth in SEQ ID NO: 1, or a fragment or analog thereof, for improving engraftment associated with transplantation.

According to another aspect, the present invention relates to an isolated polypeptide comprising the amino acid sequence set forth in SEQ ID NO: 1, or a fragment or analog thereof, for use in tissue engineering.

According to another aspect, the present invention relates to the use of a therapeutically effective amount of a polypeptide comprising the amino acid sequence set forth in SEQ ID NO: 1 or a fragment or analog thereof having the biological activity of SEQ ID NO: 1, in the preparation of a medicament for the treatment of a cardiovascular disease in a subject.

According to another aspect, the present invention relates to the use of a therapeutically effective amount of a polypeptide comprising the amino acid sequence set forth in SEQ ID NO: 1, or a fragment or analog thereof having the biological activity of SEQ ID NO: 1 for increasing the number of circulating angiogenic cells (CAC) and/or improving the function of CAC in a subject.

According to another aspect, the present invention relates to the use of a therapeutically effective amount of a polypeptide comprising the amino acid sequence set forth in SEQ ID NO: 1, or a fragment or analog thereof having the biological activity of SEQ ID NO: 1 in the preparation of a medicament for increasing the number of circulating angiogenic cells (CAC) and/or improving the function of CAC in a subject.

According to another aspect, the present invention relates to the use of a therapeutically effective amount of a polypeptide comprising the sequence set forth in SEQ ID NO: 1, or a fragment or analog thereof having the biological activity of SEQ ID NO: 1 for improving vascular remodeling and/or neovascularization in a subject.

According to another aspect, the present invention relates to the use of a therapeutically effective amount of a polypeptide comprising the sequence set forth in SEQ ID NO: 1, or a fragment or analog thereof having the biological activity of SEQ ID NO: 1 in the preparation of a medicament for improving vascular remodeling and/or neovascularization in a subject.

BRIEF DESCRIPTION OF THE FIGURES

In FIG. 1A, the percentage of CAC in S phase was evaluated by FACS analysis. In FIGS. 1B to 1F, ROS production from CAC was measured over the indicated periods of time. FIGS. 1E and 1F illustrate that UAG (6-13), a fragment of UAG, also has a protective effect on CAC from diabetes-associated oxidative stress.

In FIG. 2A, the senescence was evaluated by acidic β-gal activity on cultured CAC with AGE, UAG and AGE+UAG. In FIG. 2B, AGE-, UAG- and AGE+UAG-cultured CAC were assayed by Western blotting using the indicated antibodies. In FIG. 2C, CAC were transfected with p53 siRNA or with the scrambled sequence. In FIG. 2D, CAC from age- and sex-matched diabetic patients treated with saline or UAG were evaluated for acidic β-gal activity. In FIG. 2E, CAC recovered from diabetic patients treated as above were assayed by Western blotting using the indicated antibodies.

In FIG. 3A, a representative FACS analysis of CAC recovered from type 2 diabetic patients analyzed for the expression of CD45, CD14, CD146 and CD105. In FIG. 3B, CAC recovered after saline or UAG or AG treatment from healthy donors (N) and diabetic patients (D) were counted. In FIG. 3C, the percentage of cells in the S phase was evaluated on CAC from diabetic patients (D) or healthy subjects (N), treated with UAG, AG or with saline. In FIG. 3D, Q-RT-PCR was performed on CAC cells from type 2 diabetic patients or healthy donors cultured as above. The indicated arterial and venous markers were evaluated.

In FIG. 4A, a representative FACS analysis of CAC recovered from diabetic mice (NOD/SCID and ob/ob) or from wt mice analyzed for the expression of CD45, CD31, CD33 and KDR is reported. In FIG. 4B, blood, drawn from NOD/SCID, ob/ob and wt mice, after UAG or saline treatment was analyzed. In FIG. 4C, the percentage of cells in S phase was evaluated by FACS analysis on CAC obtained from different mouse models, treated or not with UAG. In FIG. 4D, a Q-RT-PCR was performed on CAC from mouse models cultured as above. The indicated arterial and venous markers were evaluated. In FIG. 4E, an immunohistochemical analysis of Matrigel plugs containing IL-3 and labelled CAC, recovered after implantation into SCID mice. Panel a (left) corresponds to CAC recovered after saline treatment, panel b (right) after UAG treatment. The ability of CAC to form functional vessels is reported in panel a. Black arrows indicate positive CAC cells. In FIG. 4F, Matrigel plugs recovered indicate that the majority of vessels are lined by human HLA Class I positive cells. The number of human or host derived vessels is reported in the histogram.

DETAILED DESCRIPTION

Figure 1A:
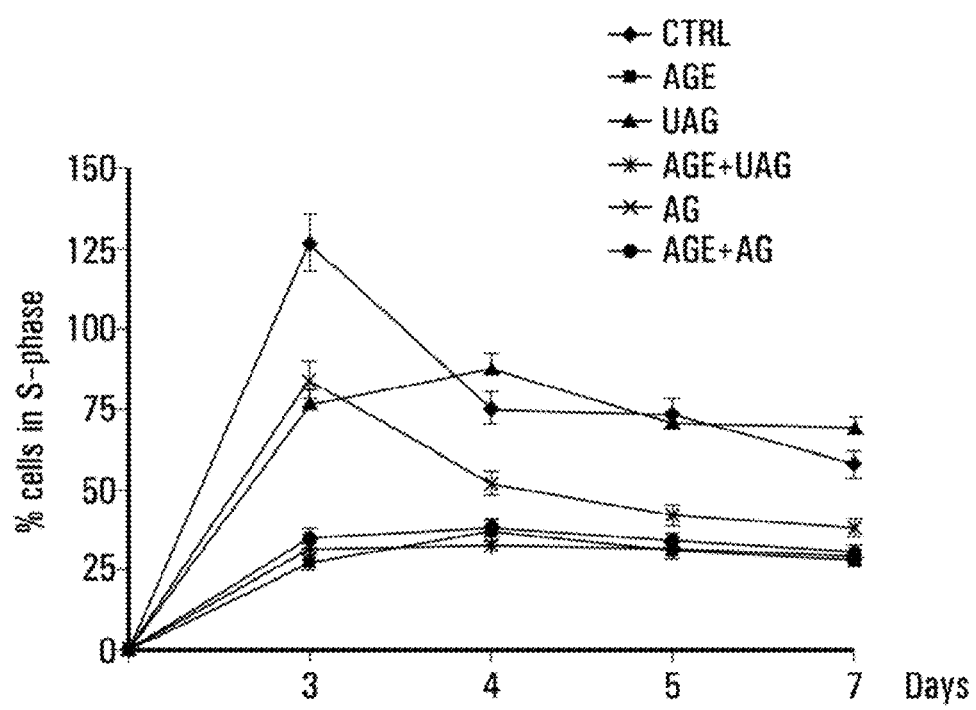
FIGS. 1A to 1F illustrate the protective effect of UAG on CAC from diabetes-associated oxidative stress.

For ease of reference, the following abbreviations and designations are used throughout:

| | |
|---|---|
| AG | ghrelin or acylated ghrelin |
| UAG | unacylated ghrelin or Des-acyl ghrelin |
| UAG (6-13) | unacylated ghrelin having residues 6 to 13 of SEQ ID NO; 1 |
| GHSR | growth hormone secretagogue receptor |
| CAC | circulating angiogenic cells |
| EPC | endothelial progenitor cells |
| AGE | advanced-glycated end product |
| BM | bone-marrow |
| VEGF | vascular endothelial growth factor |
| FACS | fluorescent-activated cell sorting |
| ROS | reactive oxygen species |

An impairment of vascular remodeling has been described in a diabetic setting (Refs. 32, 33). Both in patients with type 1 or type 2 diabetes, the number of EPC is reduced and their functional capability impaired (Refs. 15, 32). Adverse metabolic stress factors seem to mainly contribute to the impaired functional activity and to the reduced CAC recruitment into sites of arterial injury (Refs. 15, 34).

The induction of vascular growth represents an attractive therapeutic strategy in several pathological conditions. The finding that cardiovascular risk factors, such as diabetes or obesity, reduce the availability of EPC, restricts the ability to treat with cell therapy patients who theoretically need it most.

The invention defined herein provides evidence that UAG can, inter alia, prevent metabolic stress factors and restore CAC number and functional activity as shown by the ability of UAG-treated cells to form vessels in vivo.

The present invention relates to the unexpected discovery of the effects of UAG on CAC. More particularly, it relates to the unexpected discovery that UAG mobilizes CAC, protects CAC from oxidative stress or from diabetes-associated oxidative stress, reduces CAC accelerated onset of senescence and restores CAC functional activity, increases CAC number, prevents ROS production in CAC both in physiological conditions and in diabetes setting, binds to CAC and/or rescues functional impairment of CAC.

Thus, this study provides evidence that UAG can be used as a novel therapeutic strategy to improve or ameliorate impaired vascular remodeling in a subject or patient with cardiovascular risk, or to treat a subject or a patient with a cardiovascular disease or an ischemic disease, to increase CAC number and improve CAC function, to improve engraftment, to improve engraftment associated with or following transplantation of, for example, an organ or part thereof, to be used in or to facilitate in vitro or ex vivo tissue engineering, such as, but not limited to, blood vessels engineering, to improve wound healing, to improve wound healing in diabetic patients, such as diabetic patients suffering from diabetic ulcers.

Unless defined otherwise, all technical and scientific terms used herein have the same meaning as commonly understood by one of skill in the art to which the invention pertains.

Unacylated Ghrelin, Fragments and Analogs Thereof

For the purpose of the present invention the following terms are defined below.

In the present application, the terms "ghrelin" and "acylated ghrelin" or "AG" are used interchangeably and have the same meaning.

The term "unacylated ghrelin" or "UAG" is intended to mean peptides that have the amino acid sequence specified in SEQ ID NO: 1 (1-NH$_2$Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-28; SEQ ID NO: 1). UAG may also be referred to as UAG (1-28).

Naturally-occurring variations of unacylated ghrelin include peptides that contain substitutions, additions or deletions of one or more amino acids which result due to discrete changes in the nucleotide sequence of the encoding ghrelin gene or alleles thereof or due to alternative splicing of the transcribed RNA. It is understood that the said changes do not substantially affect the properties, pharmacological and biological characteristics of unacylated ghrelin variants. Those peptides may be in the form of salts. Particularly the acidic functions of the molecule may be replaced by a salt derivative thereof such as, but not limited to, a trifluoroacetate salt.

By "peptide", "polypeptide" or "protein" is meant any chain of amino acids, regardless of length or post-translational modification (e.g., glycosylation or phosphorylation), or chemical modification, or those containing unnatural or unusual amino acids such as D-Tyr, ornithine, amino-adipic acid. The terms are used interchangeably in the present application.

The term "fragments" or "fragments thereof" refers to amino acid fragments of a peptide such as unacylated ghrelin. Fragments of unacylated ghrelin are shorter than 28 amino acid residues. Fragments of unacylated ghrelin may therefore be 27, 26, 25, 24, 23, 22, 21, 20, 19, 18, 17, 16, 15, 14, 13, 12, 11, 10, 9, 8, 7, 6, 5 or 4 amino acid residues in length. For example, fragments of UAG may have residues 1-14 of SEQ ID NO: 1 as shown in SEQ ID NO: 2 ((UAG 1-14); Gly-Ser-Ser-Phe-Leu-Ser-Pro-Glu-His-Gln-Arg-Val-Gln-Gln);

residues 1-18 of SEQ ID NO: 1 as shown in SEQ ID NO: 3 ((UAG 1-18); Gly-Ser-Ser-Phe-Leu-Ser-Pro-Glu-His-Gln-Arg-Val-Gln-Gln-Arg-Lys-Glu-Ser);

residues 1-5 of SEQ ID NO: 1 as shown in SEQ ID NO: 4 ((UAG 1-5); Gly-Ser-Ser-Phe-Leu);

residues 17-28 of SEQ ID NO: 1 as shown in SEQ ID NO: 5 ((UAG 17-28); Glu-Ser-Lys-Lys-Pro-Pro-Ala-Lys-Leu-Gln-Pro-Arg);

residues 6-13 of SEQ ID NO: 1 as shown in SEQ ID NO: 6 ((UAG 6-13); Ser-Pro-Glu-His-Gln-Arg-Val-Gln);

residues 8-13 of SEQ ID NO: 1 as shown in SEQ ID NO: 7 ((UAG 8-13); Glu-His-Gln-Arg-Val-Gln) or residues 8-12 of SEQ ID NO: 1 as shown in SEQ ID NO: 8 ((UAG 8-12); Glu-His-Gln-Arg-Val) or analogs thereof. Any other fragments of UAG that preserve the biological activity of UAG are encompassed by the present invention. Some UAG fragments have been reported in U.S. patent application serial publication number US 20080312133 and in WO/2008/145749.

The survival effect of UAG (6-13) (SEQ ID NO: 6), UAG (8-13) (SEQ ID NO: 7), UAG (8-12) (SEQ ID NO: 8), UAG (8-11) (SEQ ID NO: 12), UAG (9-12) (SEQ ID NO: 9) and UAG (9-11) (SEQ ID NO: 10) was assessed in cytokine-treated HIT-T15 β-cells. As expected, the cytokines (IFN-γ/TNF-α/IL-1β) (3) strongly reduced cell survival with respect to normal culture conditions (serum containing medium). UAG (6-13) (SEQ ID NO: 6), at all the concentrations tested (1 nM to 100 nM) and particularly at 100 nM, potently inhibited cytokine-induced cell death by increasing cell survival up to values similar to or even greater than those observed in the presence of serum. Interestingly, the survival effect of UAG (6-13) (SEQ ID NO: 6) was comparable to that of full length UAG (1-28) (SEQ ID NO: 1).

Under the same experimental condition, UAG (8-13) (SEQ ID NO: 7), although less than UAG (6-13) (SEQ ID NO: 6), showed significant protective effect at all the concentrations examined, whereas UAG (8-12) (SEQ ID NO: 8) displayed significant, although reduced protection, only at 10 nM and 100 nM. The protective effects of peptides UAG (8-13) (SEQ ID NO: 7) and UAG (8-12) (SEQ ID NO: 8) were found similar to those of UAG (1-14) (SEQ ID NO: 2) and UAG (1-18) (SEQ ID NO: 3). A peptide made of the inverse sequence of UAG (1-14) (SEQ ID NO: 2) and named UAG (14-1) (SEQ ID NO: 11), was used as negative control for these experiments. With regard to UAG (8-11) (SEQ ID NO: 12), UAG (9-12) (SEQ ID NO: 9) and UAG (9-11) (SEQ ID NO: 10), MTT results indicated that UAG (8-11) (SEQ ID NO: 12) exerted significant survival effect only at 100 nM and UAG (9-12) (SEQ ID NO: 9) significantly increased cell survival at both the concentrations tested (1 and 100 nM). These effects were however lower than those of UAG (6-13) (SEQ ID NO: 6). UAG (9-11) (SEQ ID NO: 10) had no significant effect at both concentrations tested.

In some aspects of the invention, the polypeptides are used in a form that is "purified", "isolated" or "substantially pure". The polypeptides are "purified", "isolated" or "substantially pure" when they are separated from the components that naturally accompany them. Typically, a compound is substantially pure when it is at least 60%, 65%, 70%, 75%, 80%, 85%, 90%, 95%, 96%, 97%, 98%, or 99%, by weight, of the total material in a sample.

The term "analog of unacylated ghrelin", "analog of fragments of unacylated ghrelin" or "analogs thereof" refers to both structural and functional analogs of unacylated ghrelin or fragments thereof which are, inter alia, capable of replacing UAG in the biological function of UAG as described in the present application, such as, but not limited to, in the prevention and treatment of cardiovascular diseases, in protecting CAC cells from oxidative stress or from diabetes-associated oxidative stress, promoting vascular remodeling and neovascularization, increasing CAC number, improving CAC function, protecting CAC from oxidative stress, preventing ROS production in CAC both in physiological conditions and in diabetes setting, protecting against oxidative stress associated with inhibition of the accelerated onset of CAC senescence, binding to CAC membranes, and increase mobilization of CAC and/or rescue functional impairment of CAC, as described in the present application. Hence such structural and functional analogues will be useful for realizing therapeutic benefits in medical conditions as described in the present application.

Simple structural analogs comprise peptides showing homology with unacylated ghrelin as set forth in SEQ ID NO: 1 or homology with any fragment thereof. An example of an analog of ghrelin is an isoform of ghrelin-28 (SEQ ID NO: 1), des Gln-14 Ghrelin (a 27 amino acid peptide possessing serine 3 modification by n-octanoic acid) which is shown to be present in stomach. It is functionally identical to ghrelin in that it binds to GHSR-1a with similar binding affinity, elicits $Ca^{2+}$ fluxes in cloned cells and induces GH secretion with similar potency as Ghrelin-28. It is expected that UAG also has a des Gln-14 UAG that is functionally identical to UAG.

Preferred analogs of UAG and preferred analogs of fragments of UAG are those that vary from the native UAG sequence or from the native UAG fragment sequence by conservative amino acid substitutions; i.e., those that substitute a residue with another of like characteristics. Typical substitutions include those among Ala, Val, Leu and Ile; among Ser and Thr; among the acidic residues Asp and Glu; among Asn and Gln; among the basic residues Lys and Arg; and among the aromatic residues Phe and Tyr. Particularly preferred are analogs in which several, for example, but not limited to, 5-10, 1-5, or 1-2 amino acids are substituted, deleted, or added in any combination. For example, the analogs of UAG may differ in sequence from UAG by 1, 2, 3, 4, 5, 6, 7, 8, 9 or 10 amino acid substitutions (preferably conservative substitutions), deletions, or additions, or combinations thereof.

There are provided herein, analogs of the peptides of the invention that have at least 50%, 55%, 60%, 65%, 70%, 75%, 80%, 85%, 90%, 95%, 96%, 97%, 98% or 99% sequence homology with the amino acid sequences described herein over its full length, and sharing at least one of the metabolic effects or biological activity of UAG. A person skilled in the art would readily identify an analog sequence of unacylated ghrelin or an analog sequence of a fragment of unacylated ghrelin.

Analogs of UAG or analogs of fragments thereof are, for example, analogs obtained by alanine scans, by substitution with D-amino acids or with synthetic amino acids or by cyclization of the peptide. Analogs of UAG or fragments thereof may comprise a non-naturally encoded amino acid, wherein the non-naturally encoding amino acid refers to an amino acid that is not one of the common amino acids or pyrrolysine or selenocysteine, or an amino acid that occur by modification (e.g. post-translational modification) of naturally encoded amino acid (including, but not limited to, the 20 common amino acids or pyrrolysine and selenocysteine) but are not themselves incorporated into a growing polypeptide chain by the translation complex. Examples of such non-naturally-occurring amino acids include, but are not limited to, N-acetylglucosaminyl-L-serine, N-acetylglucosaminyl-L-threonine and O-phosphotyrosine.

As used herein, the term "modified" refers to any changes made to a given polypeptide, such as changes to the length of the polypeptide, the amino acid sequence, chemical structure, co-translational modification, or post-translational modification of a polypeptide.

The term "post-translational modification" refers to any modification of a natural or non-natural amino acid that occurs to such an amino acid after it has been incorporated into a polypeptide chain. The term encompasses, by way of example only, co-translational in vivo modifications, co-translational in vitro modifications (such as in cell-free translation system), post-translational in vivo modifications, and post-translational in vitro modifications. Examples of post-translational modifications are, but are not limited to, glycosylation, acetylation, acylation, amidation, carboxylation, phosphorylation, addition of salts, amides or esters, in particular C-terminal esters, and N-acyl derivatives of the peptides of the invention. The types of post-translational modifications are well known.

Certain peptides according to the present invention may also be in cyclized form, such that the N- or C-termini are linked head-to-tail either directly, or through the insertion of a linker moiety, such moiety itself generally comprises one or more amino acid residues as required to join the backbone in such a manner as to avoid altering the three-dimensional structure of the peptide with respect to the non-cyclized form. Such peptide derivatives may have improved stability and bioavailability relative to the non-cyclized peptides.

Methods for cyclising peptides are well known in the art and for example may be accomplished by disulfide bond formation between two side chain functional groups, amide or ester bond formation between one side chain functional group and the backbone α-amino or carboxyl function, amide or ester bond formation between two side chain functional groups, or amide bond formation between the backbone α-amino and carboxyl functions. These cyclisation reactions have been traditionally carried out at high dilution in solution. Cyclisation is commonly accomplished while the peptide is attached to the resin. One of the most common ways of synthesising cyclic peptides on a solid support is by attaching the side chain of an amino acid to the resin. Using appropriate protection strategies, the C- and N-termini can be selectively deprotected and cyclised on the resin after chain assembly. This strategy is widely used, and is compatible with either tert-butyloxycarbonyl (Boc) or 9-fluorenylmethoxycarbonyl (Fmoc) protocols. However, it is restricted to peptides that contain appropriate side chain functionality to attach to the solid support. A number of approaches may be used to achieve efficient synthesis of cyclic peptides. One procedure for synthesising cyclic peptides is based on cyclisation with simultaneous cleavage from the resin. After an appropriate peptide sequence is assembled by solid phase synthesis on the resin or a linear sequence is appended to resin, the deprotected amino group can react with its anchoring active linkage to produce protected cyclic peptides. In general, a final deprotection step is required to yield the target cyclic peptide.

Lactamazation, a form of cyclisation, may be performed to form a lactam bridge using Fmoc synthesis, amino acids with different protecting groups at the lateral chains may be introduced, such as, but not limited to, aspartic acid (or glutamic) protected with allyl ester at the beta ester (or gamma ester for glutamic acid) and lysine protected with allyloxy carbamate at the N-ε. At the end of the synthesis, with the N-terminus of the peptide protected with Fmoc, Boc or other protecting group different from Alloc, the allyl and alloc protecting groups of aspartic acid and lysine may be deprotected with, for example, palladium (0) followed by cyclization using PyAOP (7-Azabenzotriazol-1-yloxytris(pyrrolidino)phosphonium-hexafluorophosphate) to produce the lactam bridge.

Unless otherwise indicated, an amino acid named herein refers to the L-form. Well recognised abbreviations in the art will be used to describe amino acids, including levoratory amino acids (L-amino acids or L or L-form) and dextrorotary amino acids (D-amino acids or D or D-form), Alanine (Ala or A), Arginine (Arg or R), Asparagine (Asn or N), Aspartic acid (Asp or D), Cysteine (Cys or C), Glutamic acid (Glu or E), Glutamine (Gln or Q), Glycine (Gly or G), Histidine (His or H), Isoleucine (Ile or I), Leucine (Leu or L), Lysine (Lys or K), Methionine (Met or M), Phenylalanine (Phe or F), Proline (Pro or P), Serine (Ser or S), Threonine (Thr or T), Tryptophan (Trp or W), Tyrosine (Tyr or Y) and Valine (Val or V). An L-amino acid residue within the native peptide sequence may be altered to any one of the 20 L-amino acids commonly found in proteins or any one of the corresponding D-amino acids, rare amino acids, such as, but not limited to, 4-hydroxyproline or hydroxylysine, or a non-protein amino acid, such as P-alanine or homoserine.

UAG peptides may also be part of a fusion protein. It is often advantageous to include an additional amino acid sequence which contains secretory or leader sequences, prosequences, sequences which aid in purification such as multiple histidine residues, or an additional sequence for stability during recombinant production.

Any other analogs of UAG or fragments thereof or any other modified UAG or fragments thereof that preserve the biological activity of UAG are encompassed by the present invention.

General methods and synthetic strategies used in providing functional and structural analogs of UAG or fragments thereof are commonly used and well known in the art and are described in publications such as: "Peptide synthesis protocols" ed, M. W. Pennigton & B. M. Dunn. Methods in Molecular Biology. Vol 35. Humana Press, NJ., 1994; "Solid phase peptide synthesis" by Stewart and Young, W. h Freeman & Co., San Francisco, 1969 and Erickson and Merrifield; and "The Proteins" Vol. 2, p. 255 et seq. (Ed. Neurath and Hill), Academic Press, New York, 1976.

As used herein, the term "homology" refers to sequence similarity between two peptides while retaining an equivalent biological activity. Homology can be determined by comparing each position in the aligned sequences. A degree of homology between amino acid sequences is a function of the number of identical or matching amino acids at positions shared by the sequences so that a "homologous sequence" refers to a sequence sharing homology and an equivalent function or biological activity. Assessment of percent homology is known by those of skill in the art.

Methods to determine homology, identity and similarity of peptides are codified in publicly available computer programs. Preferred computer program methods to determine identity and similarity between two sequences include, but are not limited to, the GCG program package, BLASTP, BLASTN, and FASTA. The BLAST X program is publicly available from NCBI and other sources. The well known Smith Waterman algorithm may also be used to determine identity.

Preferred parameters for polypeptide sequence comparison include the following:

Algorithm: Needleman and Wunsch, J. Mol Biol. 48: 443-453 (1970);

Comparison matrix: BLOSSUM62 from Hentikoff and Hentikoff, Proc. Natl. Acad. Sci. USA. 89:10915-10919 (1992);

Gap Penalty: 12; Gap Length Penalty: 4.

A program useful with these parameters is publicly available as the "gap" program from Genetics Computer Group, Madison, Wis. The aforementioned parameters are the default parameters for amino acid sequence comparisons (along with no penalty for end gaps).

The polypeptides of the invention may be prepared in any suitable manner as known in the art. Such polypeptides include isolated naturally occurring polypeptides, recombinantly produced polypeptides, synthetically produced polypeptides, or polypeptides produced by a combination of these methods. Means and methods for preparing such polypeptides are well known in the art.

Certain aspects of the invention use UAG polynucleotides. These include isolated polynucleotides which encode the UAG polypeptides, fragments and analogs defined in the application.

As used herein, the term "polynucleotide" refers to a molecule comprised of a plurality of deoxyribonucleotides or nucleoside subunits. The linkage between the nucleoside subunits can be provided by phosphates, phosphonates, phosphoramidates, phosphorothioates, or the like, or by nonphosphate groups as are known in the art, such as peptoid-type linkages utilized in peptide nucleic acids (PNAs). The linking groups can be chiral or achiral. The oligonucleotides or polynucleotides can range in length from 2 nucleoside subunits to hundreds or thousands of nucleoside subunits. While oligonucleotides are preferably 5 to 100 subunits in length, and more preferably, 5 to 60 subunits in length, the length of polynucleotides can be much greater (e.g., up to 100). The polynucleotide may be any of DNA and RNA. The DNA may be in any form of genomic DNA, a genomic DNA library, cDNA derived from a cell or tissue, and synthetic DNA. Moreover, the present invention may, in certain aspects, use vectors which include bacteriophage, plasmid, cosmid, or phagemid.

The phrases "biological activity" or "biological property", or the term "activity" in reference to the polypeptides of the present invention, are used interchangeably herein and refer to the pharmacological, biological or cellular abilities of the polypeptides of the invention and include, but are not limited to, the capacity of replacing UAG in the biological functions of UAG such as but not limited to, in the prevention and/or the treatment of cardiovascular diseases, in protecting CAC cells from oxidative stress or from diabetes-associated oxidative stress, in promoting vascular remodeling and neovascularization, in increasing CAC number, in improving CAC function, in protecting CAC from oxidative stress, in preventing ROS production in CAC both in physiological conditions and in diabetes setting, in protecting against oxidative stress associated with inhibition of the accelerated onset of CAC senescence, in binding to CAC membranes, and in increasing mobilization of CAC and/or rescuing functional impairment of CAC.

Therapeutic Uses and Treatments

In one aspect, the present invention provides a method for treating subjects such as patients at risk of having or having a cardiovascular disease or an ischemic disease. The present invention also provides a method for improving vascular remodeling and/or neovascularization in a subject. In a further aspect, the present invention provides a method for increasing the number of CAC and improving the function of CAC in a subject. The present invention also provides for a method to improve engraftment, more particularly to improve engraftment associated with or following a transplantation of, for example, a tissue or an organ or any part thereof. The present invention also provides for a method to improve wound healing, to improve engraftment and/or to facilitate tissue engineering.

As used herein, the term "treatment" refers to both therapeutic treatments as well as to prophylactic and preventative measures. Those in need of treatment include those already with the disease or disorder or condition as well as those in which the disease, disorder or condition is to be prevented. Those in need of treatment are also those in which the disorder, disease or condition has occurred and left after-effects or scars. Treatment also refers to administering a therapeutic substance effective to improve or ameliorate symptoms associated with a disease, a disorder or a condition to lessen the severity of or cure the disease, disorder or condition, or to prevent the disease, disorder or condition from occurring.

In one aspect, the method of the invention includes the step of administering to a subject a therapeutically effective amount of a polypeptide defined herein which shares the same potential therapeutic indication as UAG itself. Such polypeptide comprises the amino acid sequence set forth in SEQ ID NO: 1, or any fragments or any analogs thereof as described above, such as, but not limited to, UAG (6-13), UAG (8-12) and UAG (8-13) fragments.

Subjects that would benefit from being administered with the polypeptides of the invention include, but are not limited to, those that are at risk of suffering or are suffering or have suffered from a cardiovascular disease or an ischemic disease. Such subjects may for example be subjects suffering from type 1 or type 2 diabetes and/or may be subjects suffering from obesity.

As used herein, the term "cardiovascular disease" refers to diseases that involve the heart or blood vessels (arteries and veins). The term refers to any disease that affects the cardiovascular system. It also refers to diseases related to atherosclerosis (arterial disease). Cardiovascular diseases include, but are not limited to, aneurysm, angina, arrhythmia, cardiomyopathy, cerebrovascular accident (stroke), cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, mitral valve prolapse, myocardial infarction (heart attack), venous thromboembolism, ischemia and wound healing.

Additionally, any subject suffering from or being at risk of suffering from vascular complications, cardiovascular diseases associated with the metabolic syndrome or syndrome X or obesity, atherosclerosis, primary artherosclerotic vascular degeneration such as central and peripheral arteriopathy, or any subject in need of vascular remodeling or in need of neovascularization would benefit from being administered with the polypeptides of the invention. As used herein, the expression syndrome X refers to a combination of medical disorders that includes the risk of developing cardiovascular diseases.

The term "oxidative stress" refers to an imbalance between the production of reactive oxygen and a biological system's ability to readily detoxify the reactive intermediates or easily repair the resulting damages.

Any subject or patient that would benefit from an increase in the CAC number and/or an improvement in CAC function would benefit from administration of the polypeptides of the invention.

CAC number refers to the amount or concentration of CAC that home from the bone marrow into sites of vascular remodeling and/or sites of noeovascularization.

CAC function refers to the property of CAC to mobilize to a site of endothelization (CAC mobilization), differentiate into endothelial cells and participate in endothelization. Improvement of CAC function refers to bringing into a more desirable condition CAC function, such as for example, improving CAC mobilization refers to bringing into a more desirable condition CAC mobilization.

Any subject in need of vascular remodeling or vascular restoration and/or in need of noeovascularization would also benefit from administration of the polypeptides of the invention.

The term "vascular remodeling" or "vascular restoration" refers to any lasting changes in the diameter, thickness, or structure of a mature blood vessel. The term "vascular remodeling" also includes collateral vessel formation. For example, in atherosclerosis, vascular remodeling acts as a compensatory mechanism to preserve blood flow in the face of plaque growth, which tends to cause stenosis or narrowing of the artery.

The term "neovascularization" refers to the formation of functional microvascular networks with red blood cell perfusion.

Improvement of vascular remodeling and/or neovascularization refers to bringing into a more desirable condition vascular remodeling and/or neovascularization.

The polypeptides of the invention are also useful to promote engraftment of, for example, cells, tissues and/or organs or parts thereof, in a transplant recipient such as an animal or a human. As used herein, the term "engraftment" refers to incorporation of grafted tissue into the body of a host. As used herein, the term "engraftment" also refers to the process in which transplanted stem cells or bone marrow cells migrate to the bone marrow and begin producing blood cells.

The polyeptides described herein are also useful in regenerative medecine or in tissue engineering to develop biological substitutes that restore, maintain, or improve tissue function of a whole organ or a part thereof, such as, for example, the heart, blood vessels, bone marrow, or the like. The expression "tissue engineering" also refers to the production of natural or synthetic organs and tissues that can be implanted as fully functional units or may develop to perform necessary functions following implantation. The methods of regenerative medecine or tissue engineering are known to those of skill in the art.

The polypeptides defined herein are also useful for improving wound healing. In a specific but non-limiting example, the polypeptides defined herein are also useful for improving wound healing in diabetic patients such as improving healing of diabetic ulcers.

The term "metabolic disorders" refers to, but is not limited to, disorders of carbohydrate metabolism, disorders of amino acid metabolism, disorders of organic acid metabolism (organic acidurias), disorders of fatty acid oxidation and mitochondrial metabolism, disorders of porphyrin metabolism, disorders of purine or pyrimidine metabolism, disorders of steroid metabolism, disorders of mitochondrial function, disorders of peroxisomal function and lysosomal storage disorders.

The term "metabolic syndrome" refers to a combination of medical disorders that increase one's risk for cardiovascular disease and diabetes.

It is a further aspect of the present invention to provide for any pharmaceutical composition incorporating at least one of the polypeptides as defined herein.

For therapeutic and/or pharmaceutical uses, the polypeptides as defined herein may be formulated for, but not limited to, intravenous, subcutaneous, transdermal, topical, oral, buccal, sublingual, nasal, inhalation, pulmonary, or parenteral administration according to conventional methods. Intravenous injection may be by bolus or infusion over a conventional period of time. The polypeptides as defined herein may also be administered directly to a target site within a subject e.g., by biolistic delivery to an internal or external target site or by catheter to a site in an artery.

Active ingredients, such as the polypeptides defined herein, to be administered orally as a suspension can be prepared according to techniques well known in the art of pharmaceutical formulation and may contain, but not be limited to, microcrystalline cellulose for imparting bulk, alginic acid or sodium alginate as a suspending agent, methylcellulose as a viscosity enhancer, and sweeteners/flavoring agents. As immediate release tablets, these compositions may contain, but are not limited to microcrystalline cellulose, dicalcium phosphate, starch, magnesium stearate and lactose and/or other excipients, binders, extenders, disintegrants, diluents and lubricants. The active ingredients may be administered by way of a controlled-release delivery system.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

The polypeptides of the invention may be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, well known in the art.

The polypeptides of the invention may also be formulated for topical administration. The term "topical" as used herein includes any route of administration that enables the compounds to line the skin or mucosal tissues. Topical administration of the polypeptides defined herein is useful for example, to improve wound healing or to improve wound treatment or for in situ treatment in a subject.

The formulation suitable for topical application may be in the form of, for example, cream, lotion, solution, gel, ointment, paste, plaster, paint, bioadhesive, or the like, and/or may be prepared so as to contain liposomes, micelles, microparticles and/or microspheres. The formulation may be aqueous, i.e., contain water, or may be nonaqueous and optionally used in combination with an occlusive overlayer so that moisture evaporating from the body surface is maintained within the formulation upon application to the body surface and thereafter.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum delivery of the polypeptides defined herein, and, preferably, will provide for other desired characteristics as well, e.g., emolliency or the like. Creams, as also well known in the art, are viscous liquids or semisolid emulsions, either oil-in-water or water-in-oil. Cream bases are water-washable, and contain an oil phase, an emulsifier, and an aqueous phase. As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Lotions, which are preferred for delivery of cosmetic agents, are preparations to be applied to the skin surface without friction, and are typically liquid or semi-liquid preparations in which solid particles, including the active agent, are present in a water or alcohol base. Lotions are usually suspensions of solids. Pastes are semisolid dosage forms in which the active agent is suspended in a suitable base. Depending on the nature of the base, pastes are divided between fatty pastes or those made from a single-phase aqueous gels. Plasters are comprised of a pasty mixture that is spread on the body, either directly or after being saturated into a base material such as cloth. Formulations of the invention, may be dissolved or dispersed within the plaster to make a medicated plaster. Bioadhesives are preparations that adhere to surfaces of body tissues. Polymeric bioadhesive formulations are well known in the art.

Formulations may also be prepared with liposomes, micelles, microparticles and/or microspheres. Liposomes are microscopic vesicles having a lipid wall comprising a lipid bilayer, and can be used as drug delivery systems. Micelles are known in the art to be comprised of surfactant molecules arranged so that their polar headgroups form an outer spherical shell, while the hydrophobic, hydrocarbon chains are oriented towards the center of the sphere, forming a core. Microparticles are particulate carrier systems in the micron size range, normally prepared with polymers, which can be used as delivery systems for drugs or vaccines that are usually trapped within the particles. Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids.

Preparation of formulations suitable for topical administration are well known in the art and described in the pertinent texts and literature.

In general, pharmaceutical compositions will comprise at least one of the polypeptides of the invention together with a pharmaceutically acceptable carrier which will be well known to those skilled in the art. The compositions may further comprise for example, one or more suitable excipients, diluents, fillers, solubilizers, preservatives, salts, buffering agents and other materials well known in the art depending upon the dosage form utilized. Methods of composition are well known in the art.

In the present context, the term "pharmaceutically acceptable carrier" is intended to denote any material, which is inert in the sense that it substantially does not have any therapeutic and/or prophylactic effect per se and that are non-toxic. A pharmaceutically acceptable carrier may be added to the polypeptides of the invention with the purpose of making it possible to obtain a pharmaceutical composition, which has acceptable technical properties.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG.

Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols.

The polypeptides used for in vivo administration must be sterile. This may be accomplished by filtration through sterile filtration membranes, prior to or following lyophilization and reconstitution. The polypeptidesordinarily will be stored in lyophilized form or in solution. Therapeutic polypeptide compositions generally are placed into a container having a sterile access port, for example, an intravenous solution bag or vial having a stopper pierceable by a hypodermic injection needle.

For use in the methods defined herein, the invention also provides an article of manufacture or a commercial package or kit, comprising: a container, a label on the container, and a composition comprising the polypeptides of the invention as an active agent within the container when used at the indicated level, wherein the composition is effective for, inter alia, the treatment of a cardiovascular disease and/or for improving vascular remodeling or neovascularization and/or increasing CAC number and improving CAC function and/or to improve wound healing, and/or to be used in or facilitate engraftment and/or tissue engineering. The label on the container indicates for what the composition can be used.

A "therapeutically effective amount" refers to an amount effective, at dosages and for periods of time necessary, to achieve the desired therapeutic result. A therapeutically effective amount of the peptides noted herein may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the onset of a condition related to insulin levels and/or activity. A prophylactically effective amount can be determined as described above for the therapeutically effective amount. For any particular subject, specific dosage regimens may be adjusted over time according to the individual need and the professional judgement of the person administering or supervising the administration of the compositions.

For example, a therapeutically effective amount or effective dose of the peptides of the invention (also referred to herein as "active compound") is an amount sufficient to improve or ameliorate impaired vascular remodeling in a subject or patient with cardiovascular risk, or to treat a subject or a patient with a cardiovascular disease or an ischemic disease, to improve engraftment, to improve engraftment associated with or following transplantation of an organ or a part thereof, to be used in or to improve or facilitate in vitro or ex vivo tissue engineering, such as, but not limited to blood vessels engineering, to improve wound healing, to improve wound healing in diabetic patients, such as diabetic patients suffering from diabetic ulcers. The methods and/or assays for measuring such parameters are known to those of ordinary skill in the art.

The therapeutically effective amount of the invention will generally vary from about 0.001 µg/kg to about 10 mg/kg, more particularly from about 0.01 µg/kg to about 10 mg/kg, and even more particularly from about 1 µg/kg to about 1 mg/kg. Therapeutically effective amounts or effective doses that are outside this range but that have the desired therapeutic effect are also encompassed by the present invention.

In a one aspect, the subject noted above is a mammal, in a further aspect, a human.

Experiments and Data Analysis

In the experiments and data analysis provided below, a cardiovascular risk or disease situation was reproduced by performing some of the experiments in a diabetes setting. A person skilled in the art will appreciate that the data obtained may be extrapolated to other physiological conditions or settings which are or may be determined to be associated with impairment of CAC biological function.

UAG Effect on CAC Cell Mobilization and Metabolism

I. UAG Protects CAC From Oxidative Stress

Oxidative stress plays a major role in tissue damage (Ref. 21) and endothelial injury associated with diabetes mainly depends on the production of reactive oxygen species (ROS). The observation that UAG or AG protects endothelial cells from apoptosis (Ref. 8) led to evaluate the effect of both ghrelin isoforms on CAC biology.

Figure 1B:
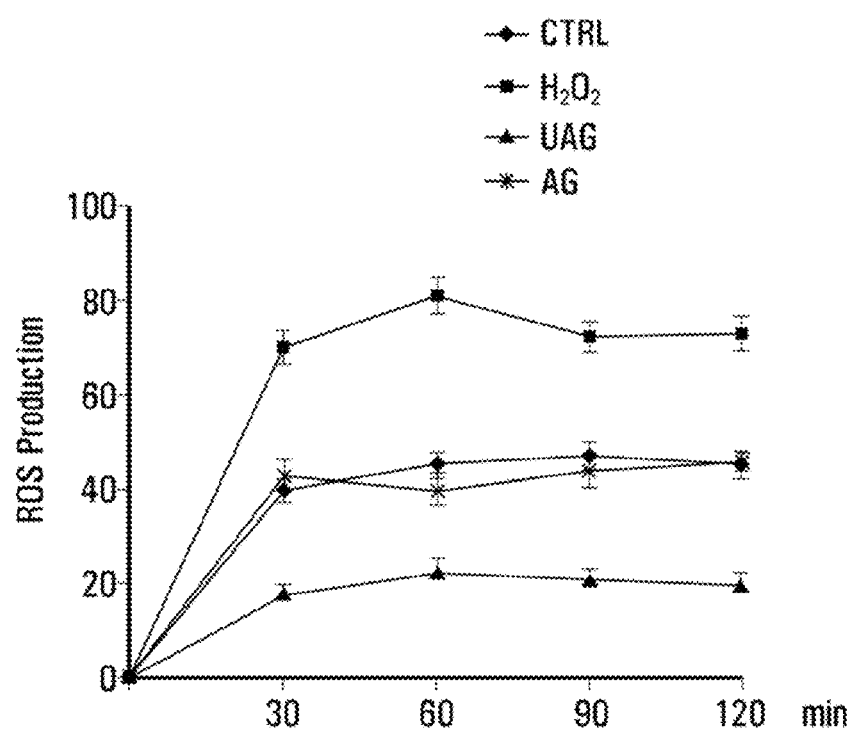
Figure 1C:
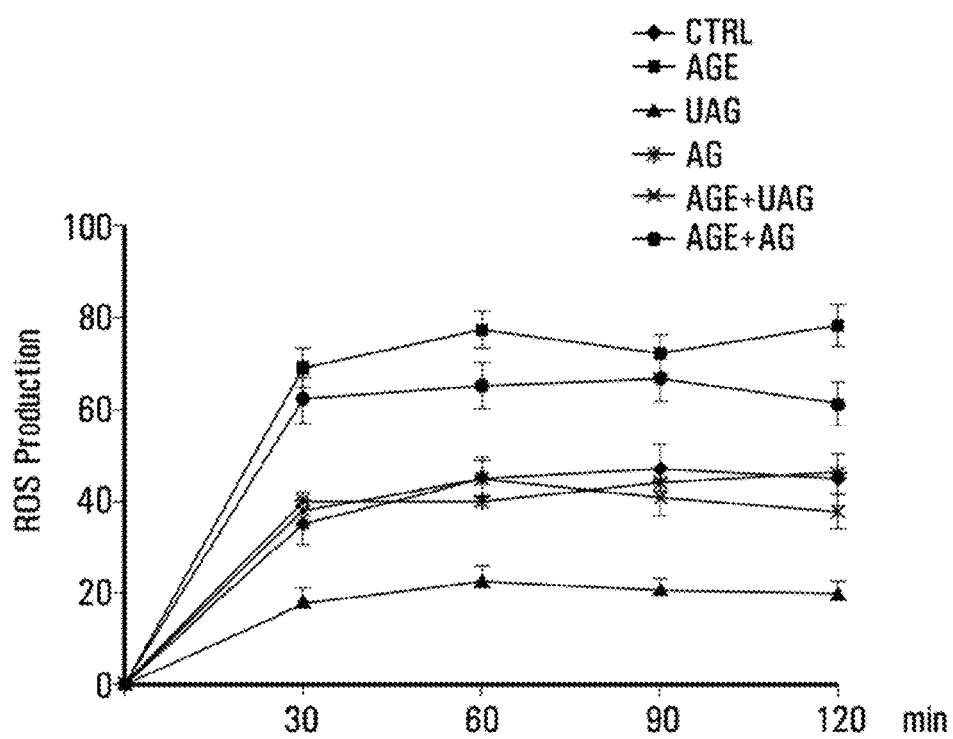
Figure 1D:
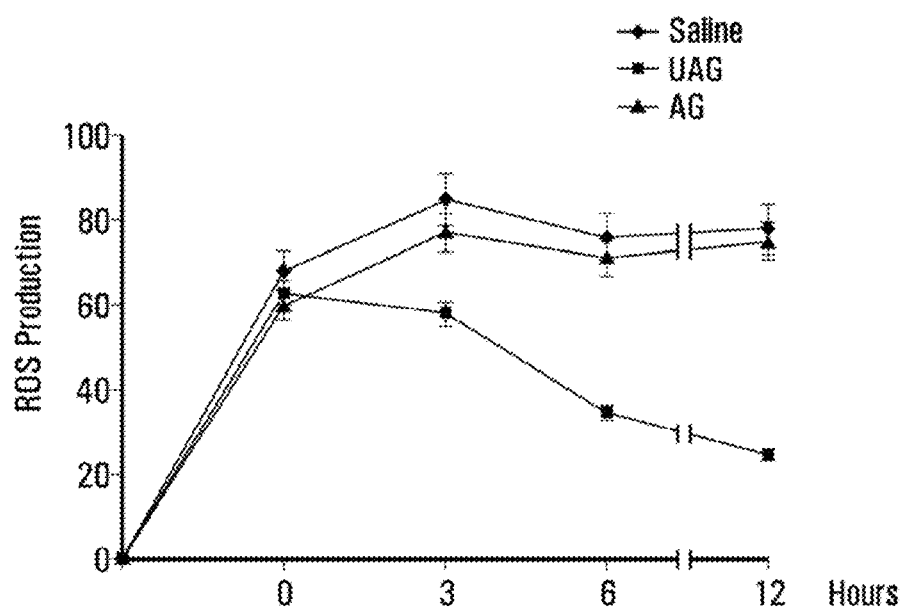
Figure 1E:
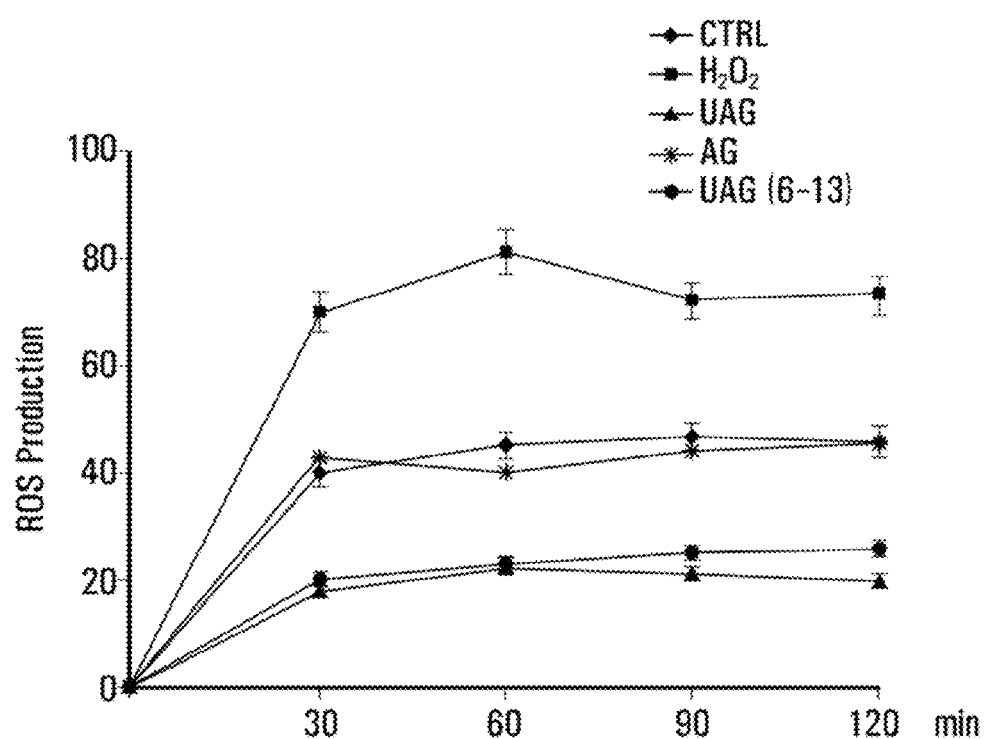
Figure 1F:
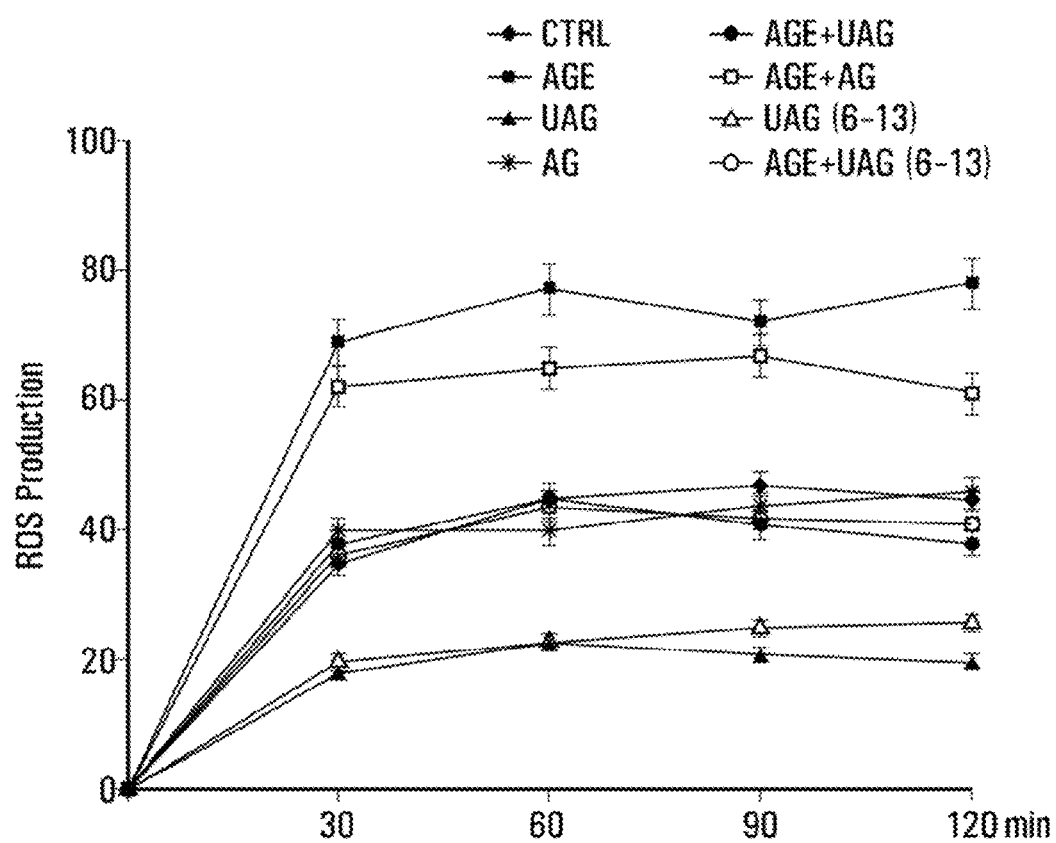

First, cell-cycle progression in response to UAG and AG was evaluated. As shown in FIG. 1A, UAG, but not AG, was able to induce a significant increase in the percentage of cells in S phase, and this effect was still evident after 7 days of culture. To investigate whether this effect relies on inhibition of baseline ROS production, DCF-DA assay was performed. The results, reported in FIG. 1B, reveal that UAG treatment drastically reduces the baseline level of ROS production when compared to untreated cells. A protective effect failed to be detected when AG was used (FIG. 1B). FIG. 1E reveals that a fragment of UAG, namely UAG (6-13) also reduces the baseline level of ROS production when compared to untreated cells. $H_2O_2$ was used as positive control. AGE-mediated damage signals mainly rely on ROS production (Ref. 29). As depicted in FIGS. 1C and 1F, the level of ROS production in AGE-cultured cells was reduced when cells were challenged with UAG or with UAG (6-13) fragment. Consistent with the above results, no effects could be detected with AG. To further confirm these data, CAC were isolated from type 2 diabetic patients and subjected to UAG or AG treatment. Data reported in FIG. 1D reveal that UAG, but not AG, reduced intracellular ROS production in diabetic-recovered cells.

II. UAG Prevents CAC Senescence

Apart from DNA damage, stress-caused signals also induce senescent-like growth arrest (Ref. 30). p53, p21, and pRb are the major regulators of senescence and ROS production is generally considered as an upstream signal. It was previously shown that an accelerated onset of senescence can be detected in EPC from diabetic patients (Ref. 22). The above data led to evaluate whether ROS production translates into an accelerated onset of senescence and whether UAG could rescue this effect.

Figure 2A:
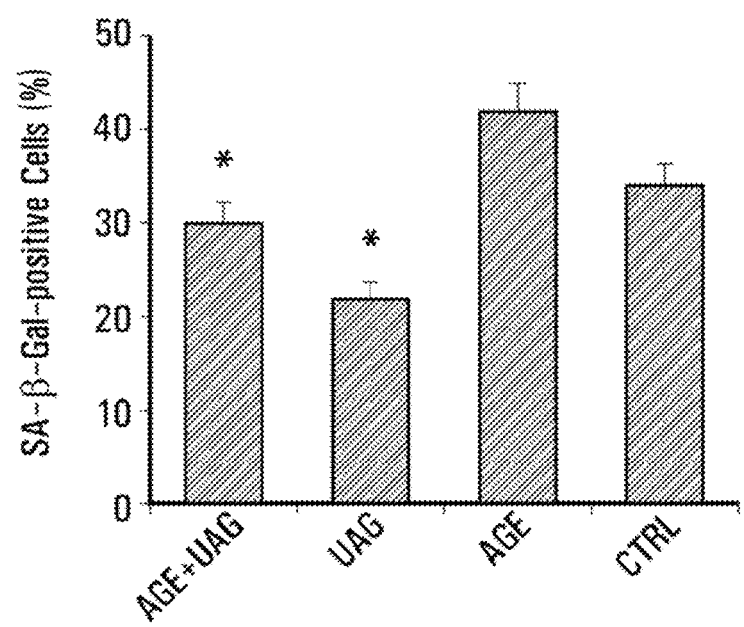
FIGS. 2A to 2E illustrate that UAG prevents CAC senescence.
Figure 2B:
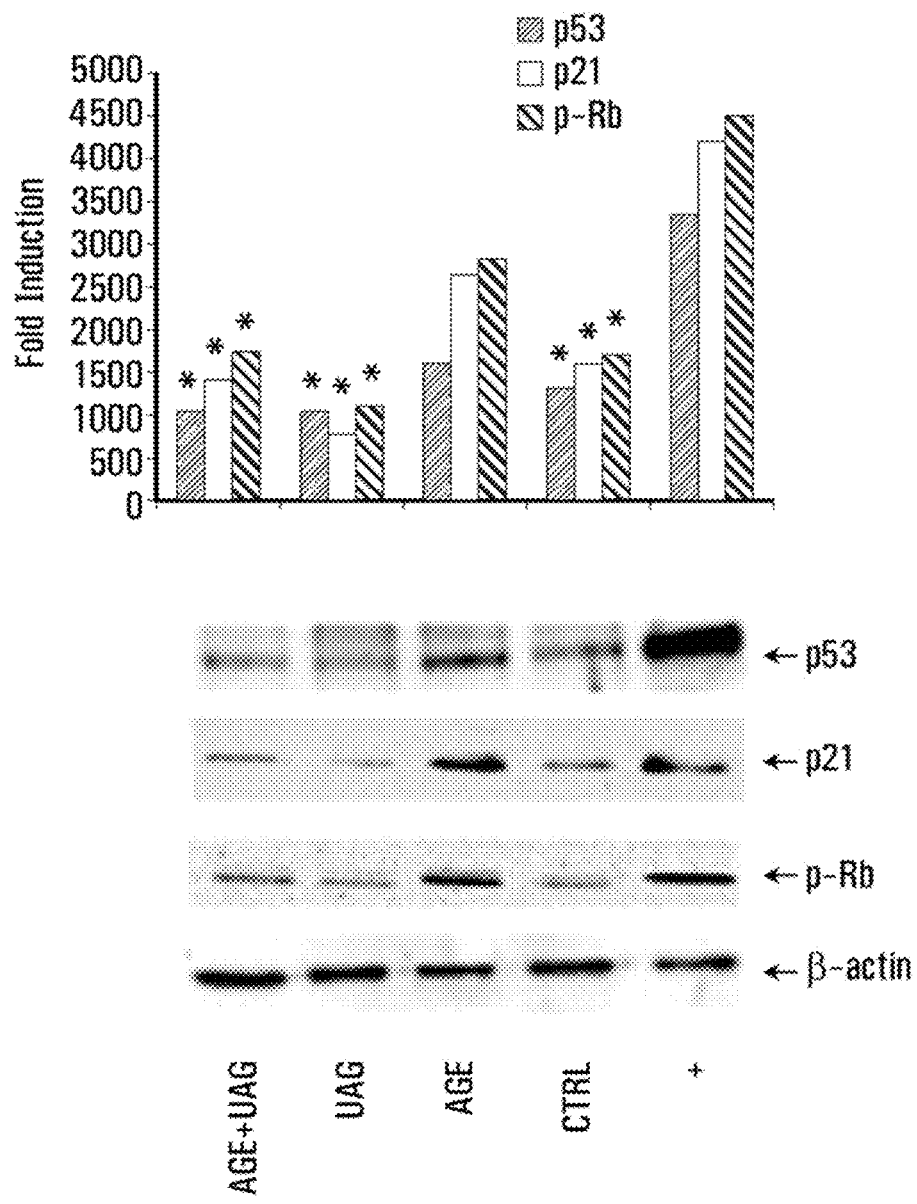
Figure 2C:
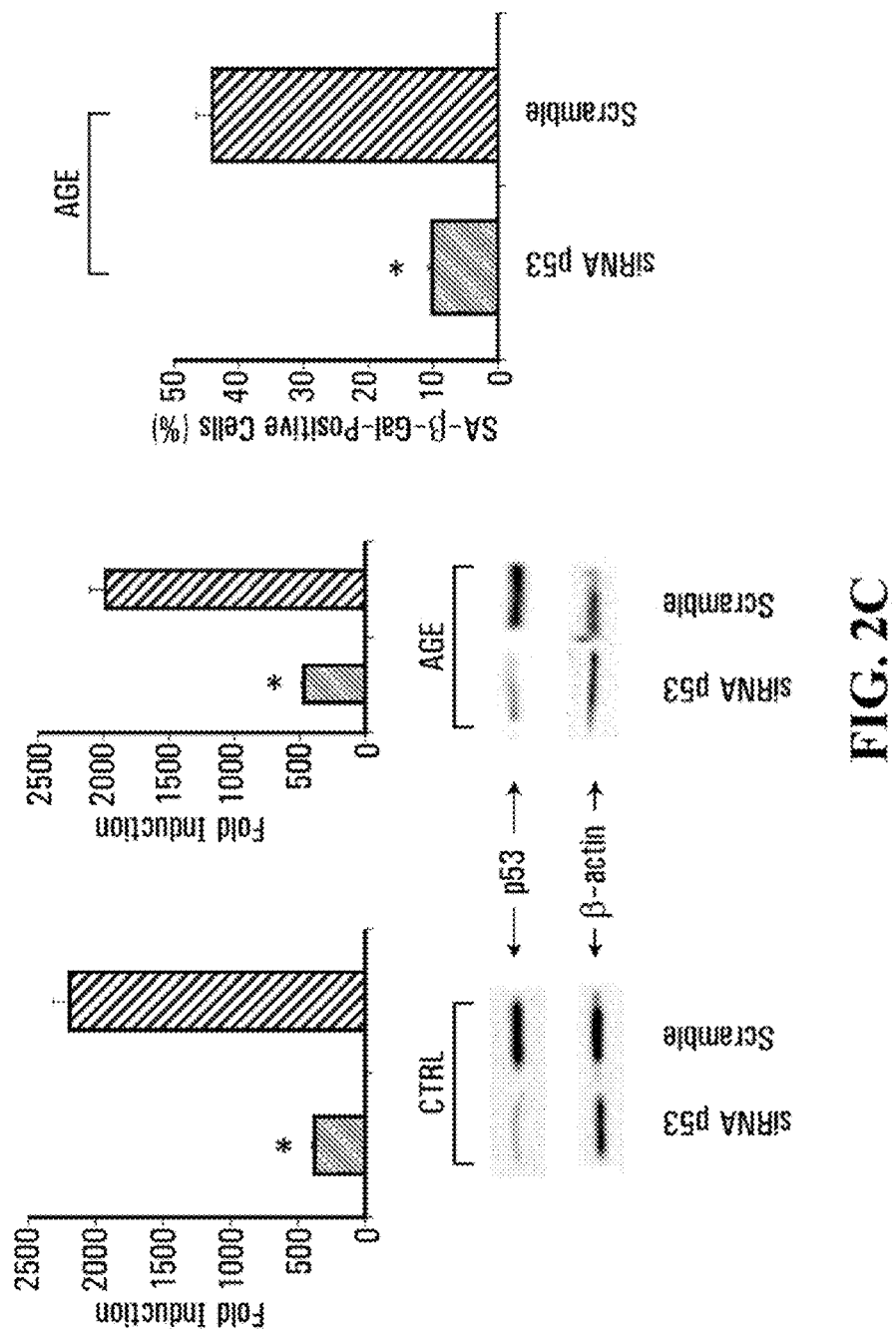

To this end, the effect of AGE treatment, alone or in combination with UAG, was first evaluated on SA-β-gal activity. Consistent with the results on ROS production, UAG was able to reduce the number of senescent cells (FIG. 2A). In addition, a significant reduction in the number of SA-β-gal positive cells could also be detected when UAG was added to AGE-cultured CAC (FIG. 2A). The role of p53, p21 and pRb in mediating this event is sustained by the observation that UAG prevented p53 accumulation, p21 expression and phosphorylation of Rb induced by AGE (FIG. 2B). In addition, AGE-induced p53 accumulation and senescent like-growth arrest were prevented by silencing p53 (FIG. 2C).

Figure 2D:
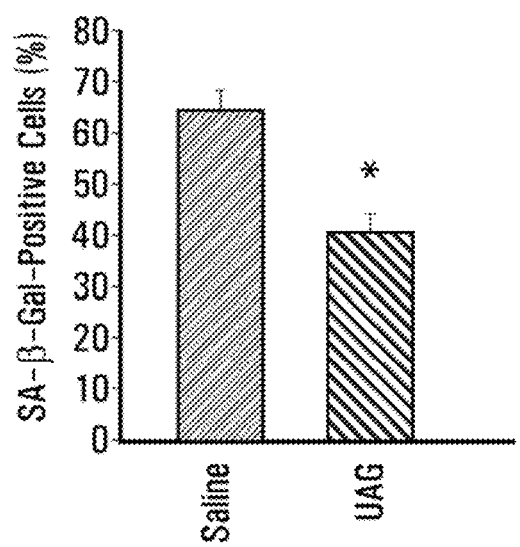
Figure 2E:
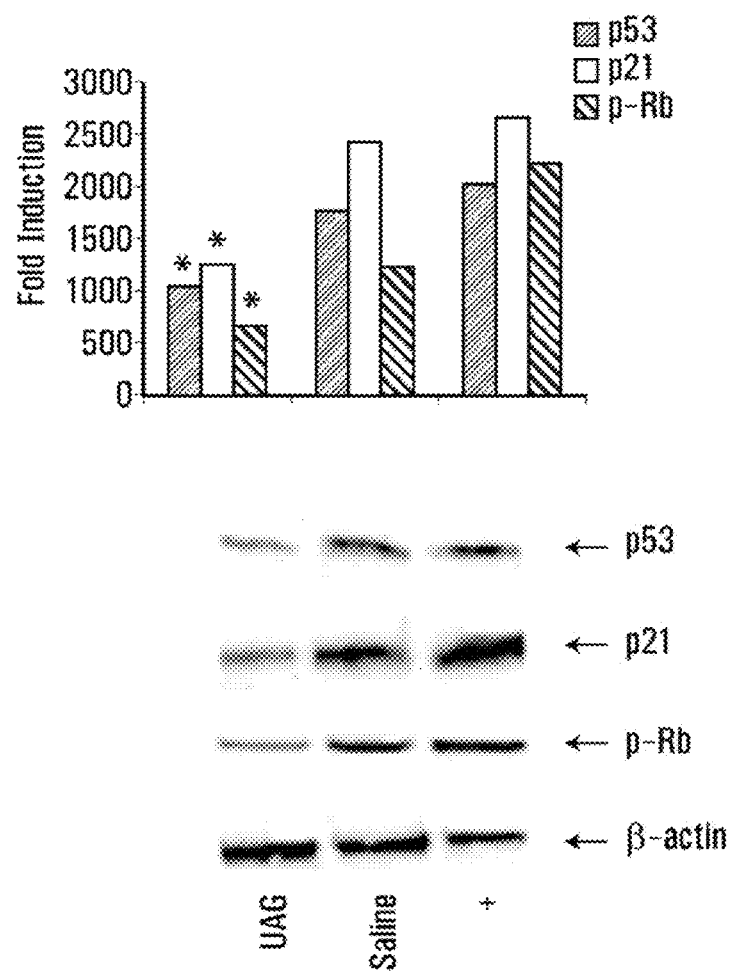

To further confirm these data, type 2 diabetic patients were subjected to UAG treatment. After 12 hours of treatment, CAC were recovered from UAG treated and untreated patients and cultured. As shown in FIGS. 2D and 2E, when administered in vivo, UAG reduced the number of senescent cells and prevented p53 accumulation, phosphorylation of Rb and p21 expression. These data further confirm that a p53-mediated signalling pathway contributes to the impaired CAC function in a diabetic setting and that UAG can prevent these events.

III. UAG Affects CAC Mobilization

CAC physiologically populate in BM and mobilize into circulation in response to microenvironment changes. Impairment in CAC mobilization has been reported in patients with cardiovascular risk factors (Refs. 19, 31).

Figure 3A:
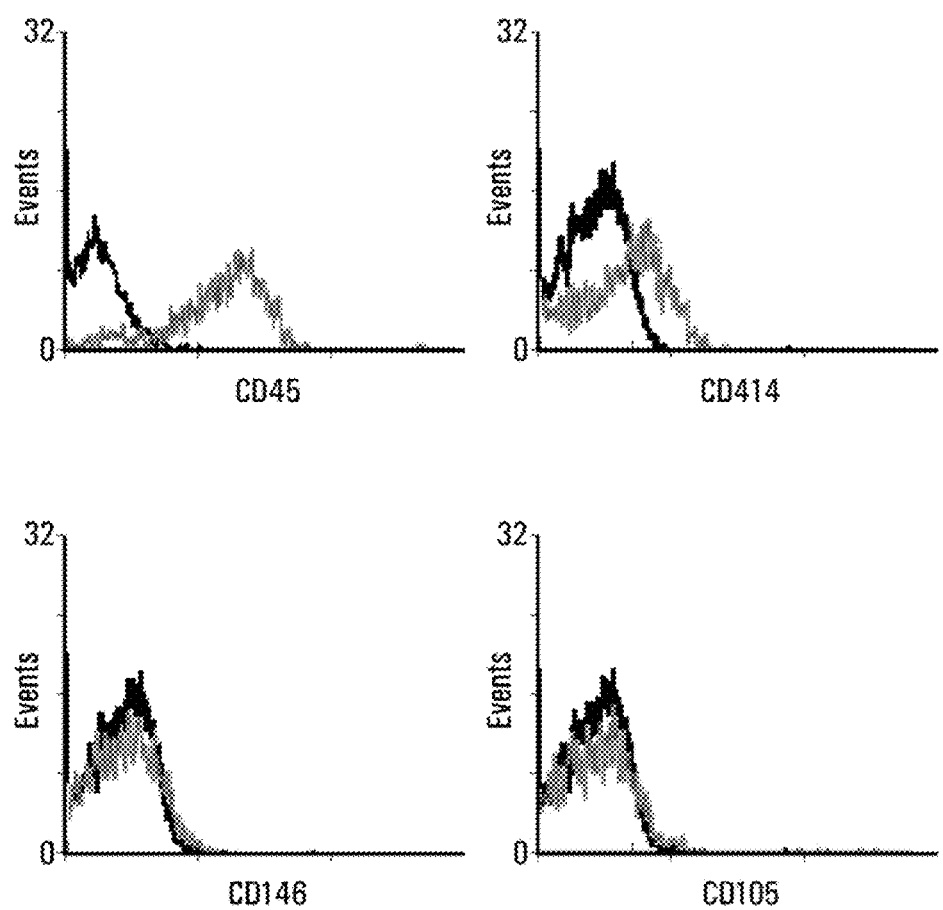
FIGS. 3A to 3D illustrate induction by UAG of CAC mobilization and arterial specification.
Figure 3B:
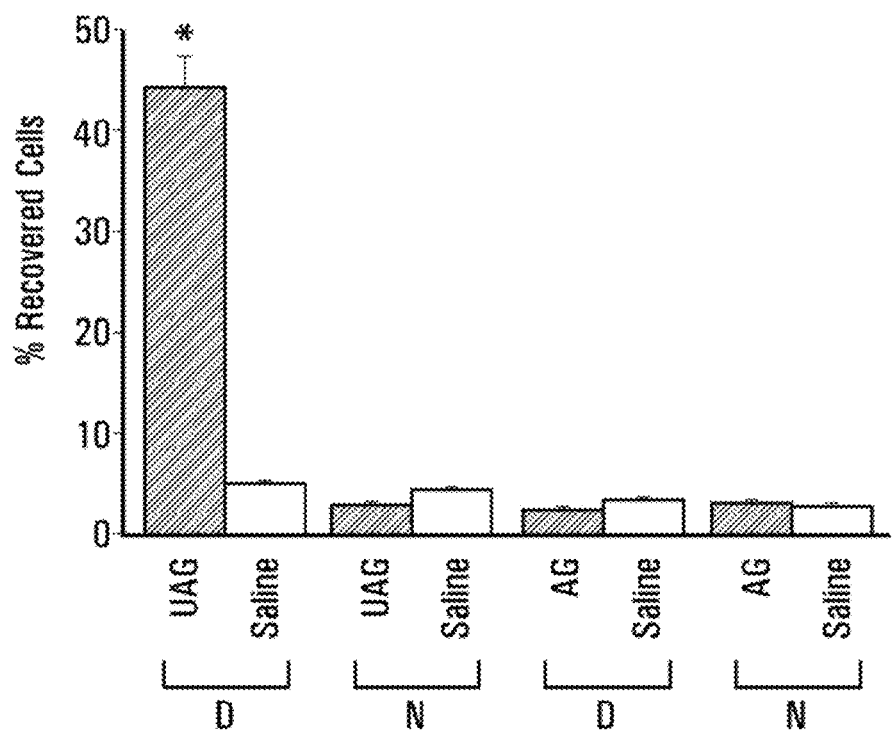

This observation led to investigate the effect of UAG treatment on BM CAC mobilization. To this end, normal subject and diabetic patients were treated with UAG or saline for 6 hours. After treatment, CAC were recovered from 4 control subjects and 4 diabetic patients, analyzed by FACS analysis and counted. As shown in FIG. 3A, FACS analysis on CAC recovered from UAG-treated patients demonstrated that indeed the recovered cells were CAC as shown by a high expression of the CD45 marker, low frequency of CD14 monocyte marker and no expression of the endothelial differentiation markers CD146 and CD105. Black lines refer to preimmune IgG used as negative control and grey lines refer to surface marker expression. Similar results were obtained when CAC from untreated diabetic patients or untreated or treated healthy subjects were analyzed (data not shown). Interestingly, UAG treatment, but not AG treatment, led to a strong increase in the number of recovered cells in diabetic patients compared to normal subjects (FIG. 3B). No statistical differences were detected in diabetic patients and controls treated with AG or saline.

Figure 3C:
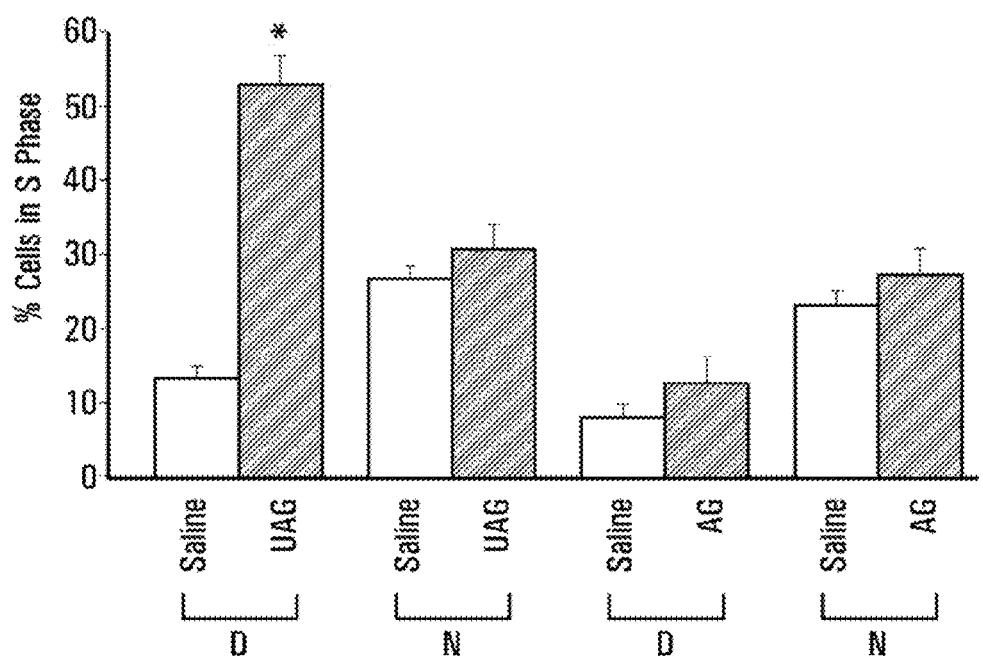
Figure 3D:
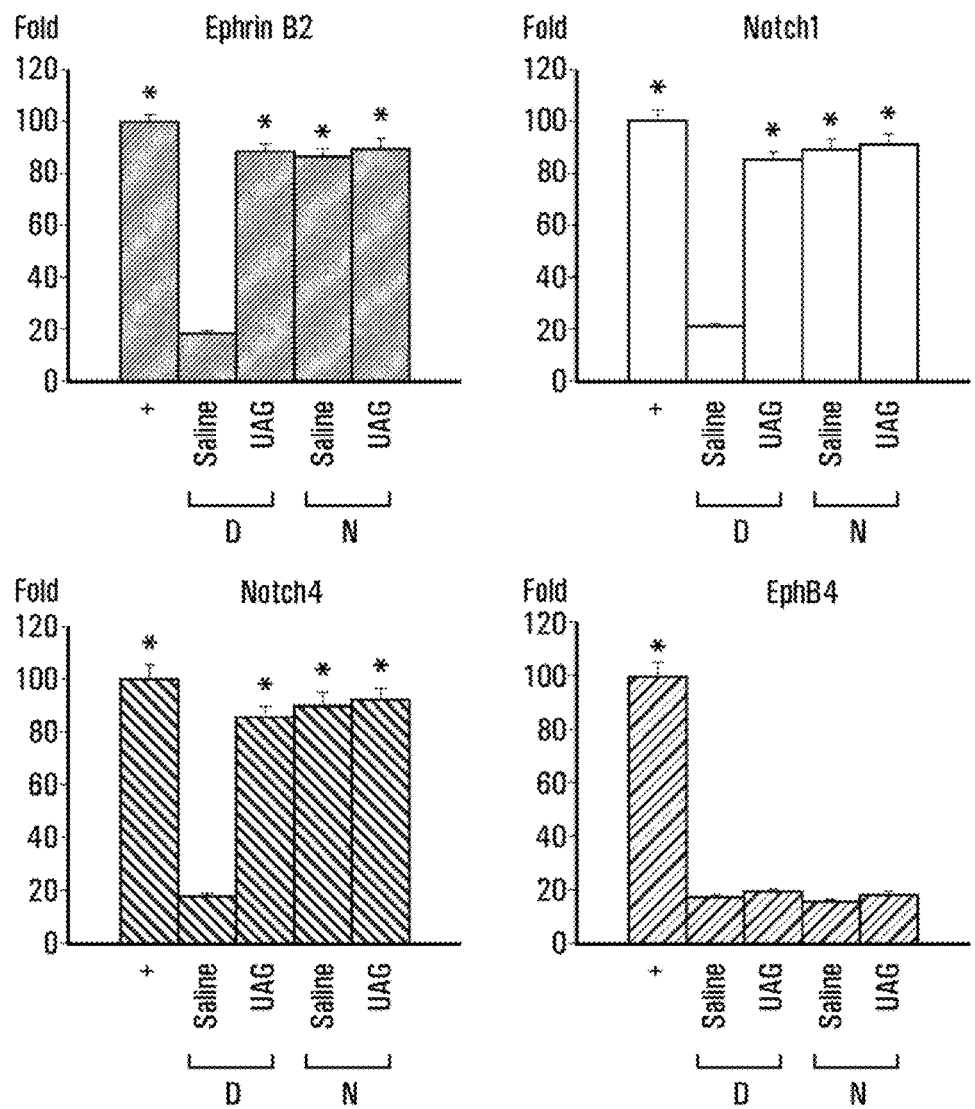

To confirm their vascular features, the cells recovered from patients and controls were cultured with IL-3; which is able to induce expansion and arterial morphogenesis of $CD45^+$ cells derived from both peripheral blood and BM (Ref. 28). As shown in FIG. 3C, cells recovered from UAG-treated diabetic patients, but not from AG-treated diabetic patients, underwent cell expansion. Moreover, as reported in FIG. 3D, when arterial morphogenesis was evaluated by quantitative (Q)-RT-PCR for arterial markers (Ephrin B2, Notch1 and Notch4) or for venous marker (EphB4), it was found that only cells obtained from UAG-treated patients were also able to undergo arterial specification. These data further indicate that diabetes-associated CAC impairment can be rescued by UAG challenge.

To further confirm data obtained by treating patients and healthy controls with UAG, two different mouse models of diabetes were used. NOD/SCID mice and ob/ob mice were treated for different time intervals with saline or UAG. The person skilled in the art will be familiar with the NOD/SCID mice and ob/ob mice models.

Figure 4A:
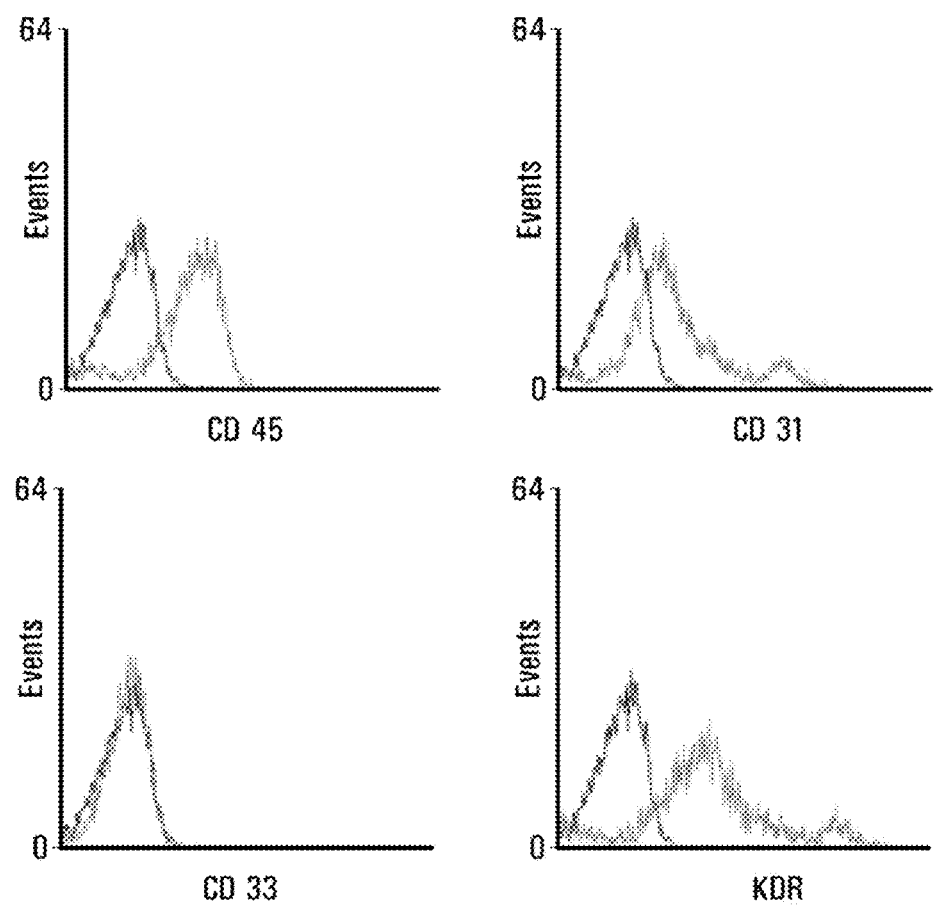
FIGS. 4A to 4F illustrate that UAG induces CAG mobilization in diabetic mice and CAC exposed to UAG act as angiogenic cells.
Figure 4B:
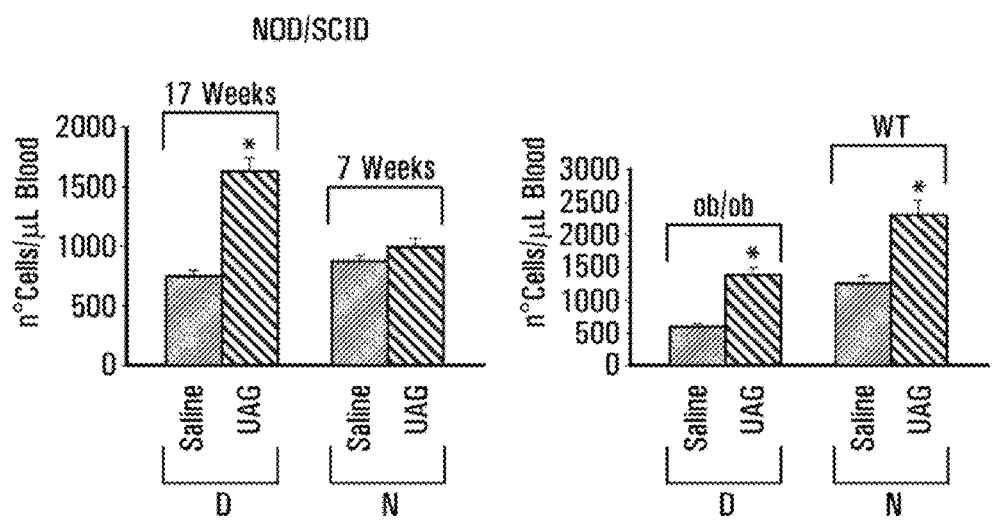
Figure 4C:
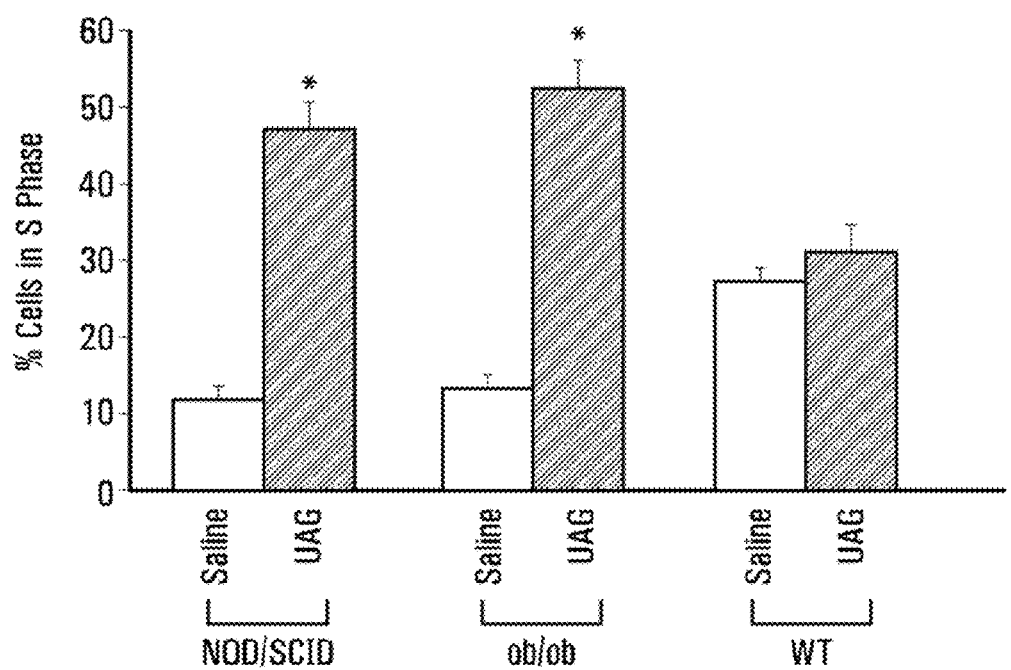
Figure 4D:
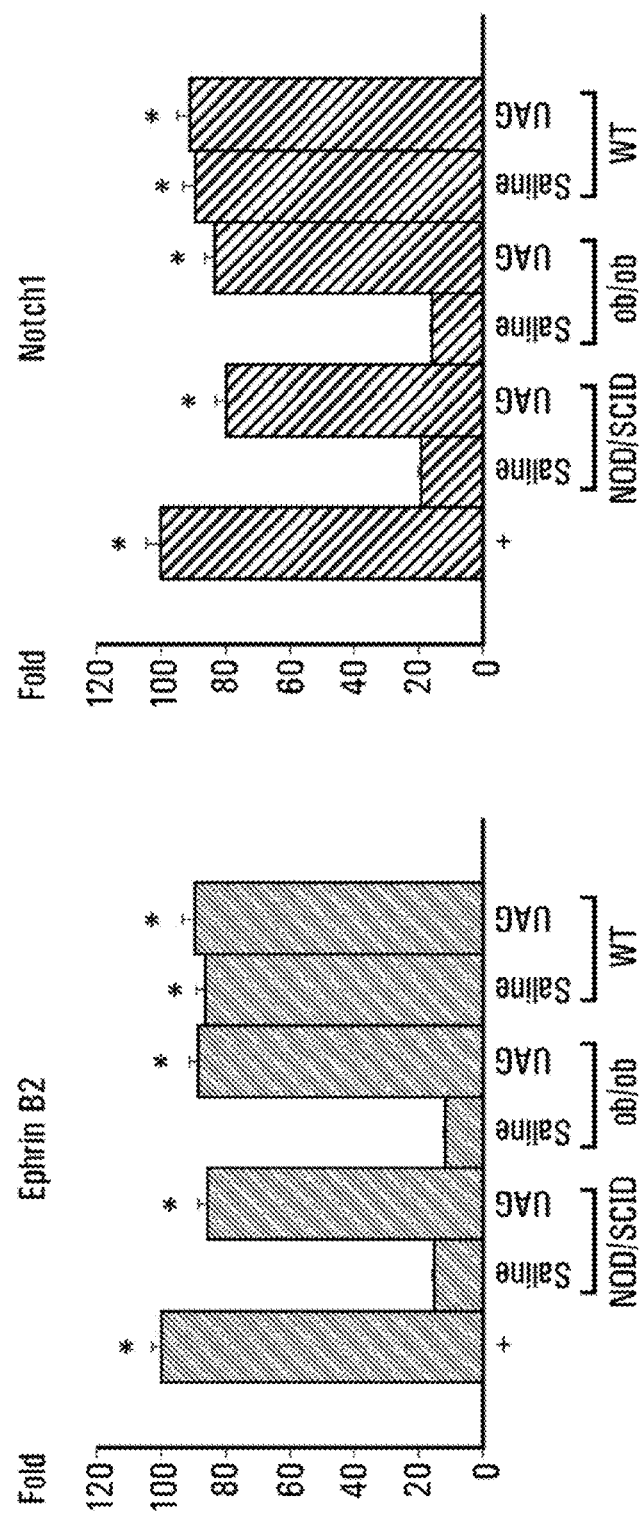

After treatment, cells were recovered, assayed by FACS analysis, counted and cultured. As shown in FIG. 4A, FACS analysis demonstrates that, as with the human counterpart, cells recovered from UAG-treated ob/ob mice expressed the CD45 marker and CD31, KDR, but not CD33. Black lines refer to preimmune IgG used as negative control and grey lines refer to surface marker expression. Similar results were obtained when CAC from untreated diabetic mice as well as untreated or treated wild-type mice were analyzed (data not shown). Moreover, unlike in not diabetic NOD/SCID mice, in diabetic NOD/SCID mice, UAG challenge was able to increase the percentage of recovered cells (FIG. 4B). The increased number of circulating CAC could also be detected in ob/ob mice challenged with UAG. Of interest, the number of cells recovered from UAG-treated ob/ob mice paralleled that of untreated wild type mice, indicating that UAG fully restores the number of CAC to normal physiological levels (FIG. 4B). Consistent with the human counterpart, CAC recovered from UAG-challenged mice could be expanded (FIG. 4C) and acquire arterial commitment when cultured in the presence of IL-3 (FIG. 4D).

UAG Effect Vascular Remodeling and Neovascularization

IV. UAG Treatment Rescues the Functional Impairment of Diabetic CAC

Figure 4E:
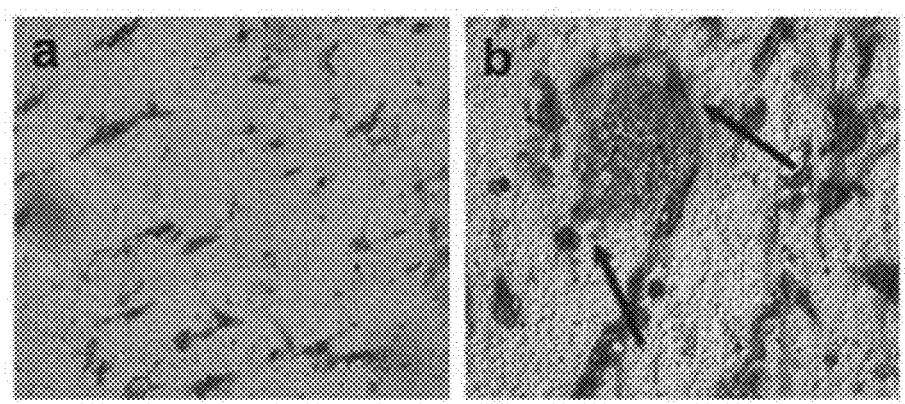
Figure 4F:
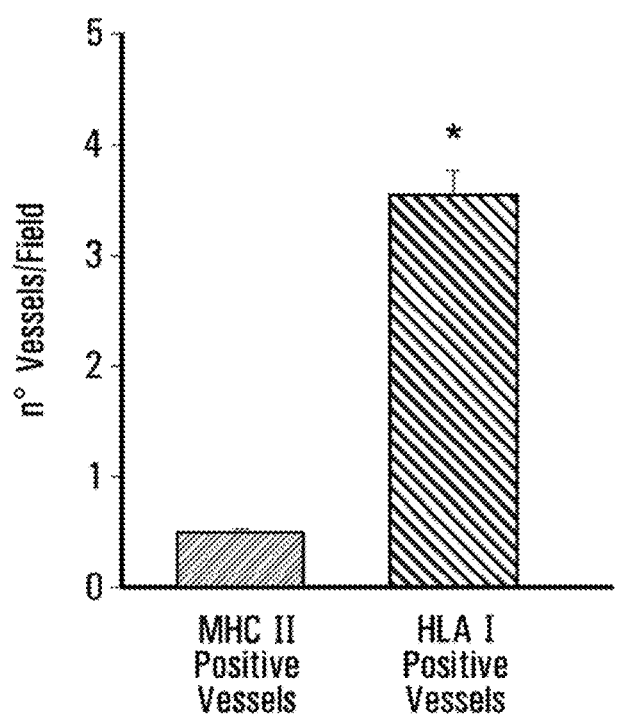

Emerging data indicate that progenitor cells are able to incorporate into existing vascular structures to form new vessels and improve perfusion (Ref. 33). To evaluate whether CAC recovered from UAG-treated diabetic patients rescue their vasculogenic capability, de novo vessel formation was assayed in vivo. To this end, Matrigel plugs containing IL-3 and CSFE-labelled CAC, recovered from untreated or UAG-treated patients, were injected into SCID mice, 15 days after injection Matrigel plugs were recovered and analyzed by immunohistochemistry. The results, reported in FIG. 4E, demonstrate that many of these labelled cells formed functional vessels as documented by erythrocytes in their lumen (FIG. 4E, panel b (right)). On the contrary no functional vessels could be detected when CAC recovered from untreated patients were used (FIG. 4E, panel a (left)). To exclude the possibility that the neo-vessels derived from vasculogenic cells of host origin, immunofluorescence assay was performed using the anti-human HLA Class I and the anti-mouse MHC II antibodies. It was found that the majority of vessels are lined by human HLA Class I positive cells (FIG. 4F). Thus, these data provide further evidence that UAG treatment improves CAC availability and vascular remodeling capability.

V. Presence of UAG Binding Sites on Human CAC

Figure 5A:
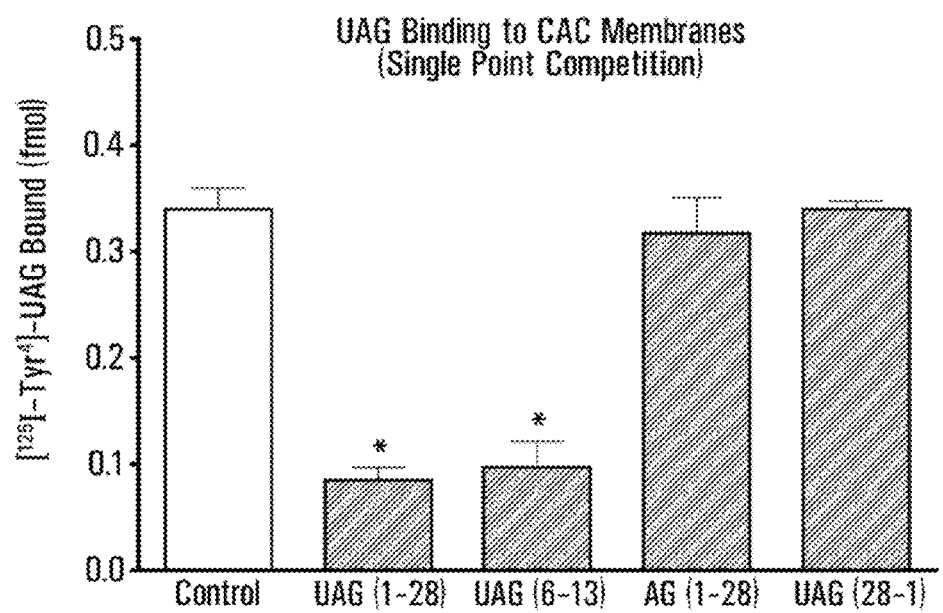
FIGS. 5A and 5B illustrate that UAG (UAG (1-28)) and UAG (6-13) fragment have binding sites on CAC membranes.

The presence of specific binding sites for UAG on CAC membranes was investigated by evaluating the ability of 100 nM unlabelled UAG (1-28) to compete with [$^{125}$I-Tyr$^4$]-UAG (0.25 nM) for such binding sites. The specificity of the binding was also tested in the presence of 100 nM AG (1-28) (acylated ghrelin), UAG (28-1), a biologically inactive ghrelin analog, and a synthetic UAG (6-13)-NH$_2$ fragment. The results of this competition binding study (FIG. 5A) revealed that the binding of [$^{125}$I-Tyr$^4$]-UAG to CAC membranes was inhibited by both UAG (1-28) and UAG (6-13), but not by AG (1-28) or UAG (28-1). The specific binding of [$^{125}$I-Tyr$^4$]-UAG (calculated as difference between binding in the absence, control, and in the presence of UAG) represented about 75% of the control value (P<0.001) and was detected either on fresh (0.25 and 0.26 fmol) or frozen-thawed (0.20 and 0.33 fmol) CAC membranes from two different cell preparations.

Figure 5B:
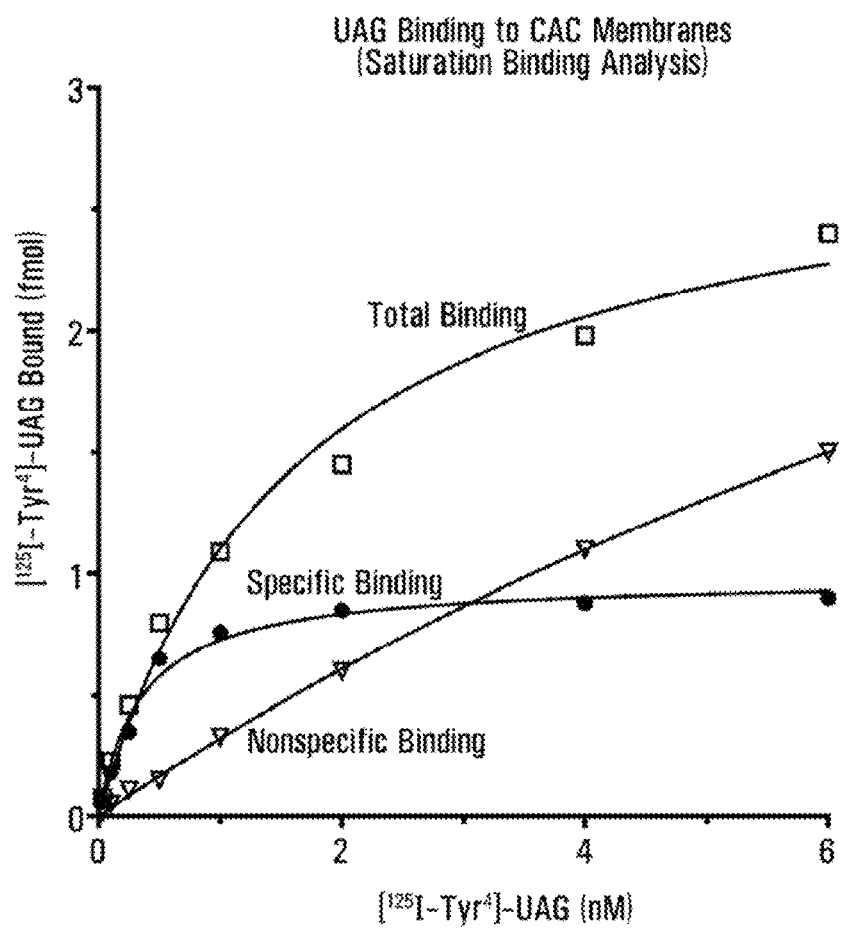

A saturation binding experiment was performed on membranes from a CAC preparation that yielded sufficient amounts of membranes for this experiment, revealed that the specific binding of the radioligand to CAC membranes was saturable (FIG. 5B), reaching a maximum at 2 nM, a concentration consistent with the physiological circulating UAG levels. Scatchard analysis of these data (data not shown) suggests the existence on CAC cells of a single class (Hill coefficient close to 1) of unacylated ghrelin binding sites with a $K_d$ of 0.48 nM and a $B_{max}$ of 10.7 fmol/mg membrane protein. These results indicate that UAG is able to bind to CAC cells with high affinity.

Materials and Technical Protocols

Patients and Controls—Blood was recovered from six type 2 diabetic patients (sex, M/F 5/1; HbA1c, 8±1.2%; age-years, 62.8±12.46; BMI, 27.1±3.22 creatinine, 1.04±0.20 mg/dl; waist circumference (cm), 98.2±7.52, total cholesterol, 192±50 mmol/L, HDL cholesterol, 46±13.98 mmol/L, LDL cholesterol, 113±39.77 mmol/L, Triglycerides, 157.5±54.23, fasting glucose 126±19.04 mg/dl no retinopathy, hypertension in 3 patients, blood pressure 141/87 mm Hg; Chol/apoB, 1.3±0.1). All were treated only with diet (no other medicaments were used by diabetic patients). Eight blood donors were used as controls (sex, M/F 4/4; age-years, 26.6±4.65; BMI 21.14±8.08, creatinine, 0.96±0.063 mg/dl, total cholesterol, 162.13±10.79 mmol/L, HDL cholesterol, 49±10.4 mmol/L, LDL cholesterol, 86.25±17.72 mmol/L, Triglycerides, 132.13±27.10, no retinopathy, no hypertension: blood pressure 125/70 mm Hg, Chol/apoB, 1.6±0.1).

All the subjects underwent the following testing session:
UAG (3.0 µg/kg/h iv. as infusion for 12 h from 0 to 12 hours);
isotonic saline (infusion from 0 to 12 hours).

All tests were performed starting at 08.30-09.00 a.m. after overnight fasting, 30 minutes after an indwelling catheter had been placed into a forearm vein by slow infusion of isotonic saline. Blood samples were taken at 0 h, 6 h and 12 h.

Reagents—M199 medium (endotoxin tested), bovine serum albumin, fetal bovine serum (FBS), glycated human albumin (AGE) were from Sigma-Aldrich (St Louis, Mo.). Bovine calf serum (endotoxin-tested) was obtained from HyClone (Logan, Utah). Trypsin was purchased from Difco. Nitrocellulose filters, horseradish peroxidase-conjugated anti-rabbit IgG and anti-mouse IgG, molecular weight markers, and chemiluminescence reagents (ECL) were from Amersham Biosciences. The acidic β-galactosidase staining kit was from Invitrogen. Peroxide hydrogen was obtained from Carlo Erba reagents. The presence of endotoxin contamination was tested by the Limulus amebocyte assay (concentration was <0.1 ng/ml). Human IL-3 was a gift from Sandoz Pharma Ltd (Basel, Switzerland). Human UAG was purchased from Phoenix Europe GmbH (Karlsruhe, Germany).

Antibodies—Monoclonal anti-p53 clone DO-1, anti-CD31, anti-Flk1/KDR, anti-CD33 FITC, anti-β-actin, anti-p21, were obtained from Santa Cruz Biotechnology, Inc. (Heidelberg, Germany). Phospho-Rb was from Cell Signaling Technology (Beverly, Mass.). Anti-mouse CD45 PE, anti-CD14 PE, anti-human CD45 FITC antisera were from Miltenyi Biotec Inc. (Auburn, Calif., USA). Anti-CD146-FITC antibody was from BioCytex (Marseille, France). Anti-CD105 FITC antibody was purchased from Tecnogenetics s.r.l. (Milano, Italy). Secondary FITC or PE antibodies were from Miltenyi Biotech Inc. and from Sigma. Anti-human HLA Class I antibody was from Sigma-Aldrich while anti-mouse MHC II antibody from Chemicon (Temecula, Calif., USA).

Isolation and Culture of CAC from Peripheral Blood Mononuclear Cells—

Peripheral-blood mononuclear cells (PB-MNC) isolated by Fycoll Histopaque 1077 (Sigma) were resuspended in 20% FBS 199 Medium and plated on fibronectin-coated dishes (Biocoat, Becton Dickinson Labware) as described by Hill et al. (Ref. 19). Human UAG studies were performed on CAC recovered from normal donors and diabetic patients. The purity of sorted cells was assessed by FACS analysis (Ref. 20). For experiments, the isolated CAC were cultured under 5% CO$_2$ at 37° C. for 4 days on 20 µg/ml fibronectin-coated dishes in EGM-2 medium containing 10% FBS, hydrocortisone, human Fibroblast Growth Factor, Vascular Endothelial Growth Factor, Insulin Growth Factor 1, ascorbic acid, human Epidermal Growth Factor, gentamicin and amphotericin-B (Cambrex, Walkersville, Md., USA) alone or in combination with 1 µM UAG and 1.2 mg/ml AGE. In selected experiments, isolated CAC were cultured in EBM-2 medium (Cambrex, Walkersville, Md., USA) supplemented with 10 ng/ml of IL-3. FACS was used to analyze their phenotype (anti-CD45, anti-CD31, anti-CD105, anti-CD14 antibodies were used) (Ref. 22).

Mobilization assay—CAC recovered from healthy subjects and diabetic patients, treated with UAG or saline for 6 h and 12 h, were evaluated. Total number of MNC was counted by 3 independent investigators. The percentage of CAC was calculated by comparing CAC obtained from diabetic patients and healthy donors, treated for 6 h and 12 h with UAG, AG or saline, to CAC recovered at time 0.

Silencing of Endogenous p53 by Small Interfering RNAs (siRNA)—To obtain inactivation of p53, CAC recovered from normal subjects cultured with or without AGE were transiently transfected by Lipofectamine PLUS™ reagent (Invitrogen) according to the vendor's instructions with the vector pSUPER retro containing p53 siRNA or a scramble p53 siRNA (control siRNA) sequences (1.5 µg) as described by Brummelkamp et al. (Ref. 23). The pSUPER retro containing p53 siRNA and the scramble p53 siRNA were gently provided by Dr. S. Soddu. 60 h later whole cell extracts were prepared, separated on 10% SDS-PAGE, and immunoblotted with anti-p53 antibody.

Detection of ROS—DCF-DA (0.5 µM final concentration) was added to CAC in the indicated culture conditions. At the indicated times, the cells were subjected to FACS analysis and processed as previously described (Ret. 22). $H_2O_2$ was used as positive control.

CAC Senescence—Senescence was evaluated by acidic β-gal activity on CAC recovered from normal subjects cultured in EGM2 medium for 4 days with UAG or AGE+UAG and saline- or UAG-treated diabetic patients (Ref. 22). Briefly, CAC were washed in phosphate-buffered saline, fixed for 3 min at room temperature in 2% paraformaldehyde, washed, and incubated for 24 h at 37° C. with fresh SA-β-gal stain solution: 1 mg/ml 5-bromo-4-chloro-3-indolyl β-D-galactopyranoside (X-gal), 5 mM/liter potassium ferrocyanide, 5 mM/liter ferricyanide, 150 mM/liter NaCl, 2 mM/liter $MgCl_2$, 0.01% sodium deoxycholate, and 0.02% Nonidet P-40. SA-β-gal-positive cells were counted manually by 3 independent investigators.

Western Blot Analysis—CAC from healthy donors cultured in the presence of UAG, in combination or not with AGE, and CAC recovered from diabetic patients treated with saline or UAG were lysed. Protein concentration was detected as previously described (Ref. 24). 50 µg of proteins were separated on SDS-polyacrylamide gels and transferred to nitrocellulose membranes. Reaction with anti-p53, anti p21 and anti-phospho-Rb antibodies and detection with an enhanced chemiluminescence detection system (Amersham Biosciences) were performed as described previously (Ref. 20).

RNA isolation and quantitative real-time PCR—CAC from diabetic patients, healthy subjects and mice treated with UAG or saline were cultured in EGM-2 medium. Human arterial and venous cells were used as a positive controls. mRNA quantification was performed by Q-RT-PCR, as previously described (Ref. 24). The relative expression of Ephrin B2, Notch1, Notch4 and EphB4 were calculated by using comparative threshold cycle methods. The human and murine primer sequences used were described (Refs. 25, 26).

Flow Cytometry—To analyze CAC cell-cycle progression, cells recovered from diabetic, healthy subjects, NOD/SCID, ob/ob and wt mice, were cultured in EBM-2 supplemented with IL-3 (10 ng/ml), FACS analysis was performed as previously described (Ref. 20). Cell surface molecules were evaluated by flow cytometry as previously described (Ref. 24). Frequency of marker-positive cells is expressed as mean±standard deviation (SD).

In Vivo Experiments

Diabetic and control mice—Mice were divided in four groups. The plasma glucose and insulin determination for each group are reported. Sixteen 6 weeks old ob/ob mice (blood glucose, 600±45 mg/dL, insulin, 5.5±0.9 ng/ml); sixteen C56BL6/J wild type mice (blood glucose, 150±18.2 mg/dL, insulin, 1±0.05 ng/ml); ten 7 weeks old NOD/SCID mice (blood glucose, 164±12.9 mg/dL, insulin 1.2±0.12 ng/ml); ten 17 weeks old NOD/SCID mice (blood glucose, 536±36.3 mg/dL, insulin 4.85±0.74 ng/ml). Animal procedures conformed to the Guide for Care and Use of Laboratory Resources (National Institutes of Health publication no. 93-23, revised 1985).

Blood glucose and serum insulin determinations—Blood glucose was measured with a One Touch II glucose meter (Lifescane, Mountain View, Calif.). Serum insulin was measured with a mouse insulin radioimmumoassay kit (Linco Research immunoassay, St. Charles, Mo.), following the manufacturers instructions.

Isolation and Culture of CAC from C57BU6J, C57BL/6J ob/ob mice and NOD/SCID mice—6 weeks old C57BL/6J (wt) and ob/ob mice, 7 and 17 weeks old NOD/SCID mice were purchased from Charles River Lab (Lecco, Italy). Animals were anesthetized by intraperitoneal injection with Avertin (100 mg/50ml ip). Blood samples were drawn from left ventricular, as described by Hoff (Ref. 27). Peripheral blood MNC were isolated by Ficoll density-gradient centrifugation. Recovered cells were washed twice Isolated cells were resuspended and were cultured on 20 µg/ml fibronectin-coated dishes in EGM-2 BulletKit Medium. In selected experiments, the isolated CAC were cultured in EBM-2 medium supplemented with 10 ng/ml of IL-3.

Mobilization assay—Mice were treated for 12 hours with UAG or saline. CAC recovered and purified as above described, were put in culture and counted by three independent investigators. The technical ratio of CAC was calculated by comparing the numbers of CAC/µL of blood drawn from left ventricular.

Matrigel-plug assay—For murine angiogenesis assay, untreated or UAG-treated CAC, obtained from type 2 diabetic patients, were counted and resuspended in DMEM ($4×10^6$ in 250 µL DMEM). Cells were chilled in ice, labelled with fluorescent dye carboxyfluorescein diacetate succinimidyl ester (CSFE, Molecular Probes), added to 250 µL Matrigel containing of IL-3 (100 ng/ml) at 4° C., and injected sc. in the abdominal paramedian region of 7 week old NOD/SCID mice (5 mice per group). After 15 days, mice were killed and Matrigel plugs were recovered, fixed in 10% buffered formalin and embedded in paraffin for immunohistochemistry.

Immunohistochemistry and immunofluorescence—For immunohistochemistry, sections from paraffin-embedded blocks of Matrigel plugs were collected onto poly-lysine-coated slides. Endogenous peroxidase activity was blocked with 6% $H_2O_2$ for 8 minutes at room temperature. To detect cells labelled with fluorescent dye CSFE, anti-Fluorescein/Oregon Green polyclonal Abs (Molecular Probes) were applied to slides overnight at 4° C. Horseradish peroxidase-labeled antirabbit Envision polymer (DakoCytomation, Carpinteria, Calif.) was incubated for 30 minutes. The reaction product was developed using 3,3-diaminobenzidine. Omission of the primary Ab or substitution with an unrelated rabbit serum IgG used as negative control. The percentage of positive cells was counted in 4 non-sequential sections for each experiment at ×40 magnification. For immunofluorescence, the samples were processed using anti-human HLA I and anti-mouse MHC II antibodies as previously described (Ref. 28). The number of MHC II or HLA I positive vessels was determined by counting 10 randomly selected fields in three different samples.

Statistical analysis—In vitro and in vivo results are representative of at least three independent experiments. The in vitro experiments were performed in triplicate. Densitometric analysis using a Bio-Rad GS 250 molecular imager was used to calculate the differences in the fold induction of protein activation or expression (* and §$p<0.05$, statistically significant between experimental and control values). Significance of differences between experimental and control values was calculated using analysis of variance with Newman-Keuls multicomparison test. Similar statistical analysis was performed in the in vivo experiments.

It is understood that the data reported in the present specification are only given to illustrate the invention and may not be regarded as constituting a limitation thereof.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All documents mentioned in the specification are herein incorporated by reference.

REFERENCE LIST

1. Kojima M, Hosoda H, Date Y, Nakazato M, Matsuo H and. Kangawa K; Ghrelin is a growth-hormone-releasing acylated peptide from stomach, *Nature* 402:656-660 (1999).

2. Gnanapavan S, Kola B, Bustin S A, Morris D G, McGee P, Fairclough P, Bhattacharya S, Carpenter R, Grossman A B and Korbonits M; The tissue distribution of the mRNA of ghrelin and subtypes of its receptor, GHS-R, in humans, *J. Clin. Endocrinol. Metab.* 87:2988-2991 (2002).

3. Howard A D, Feighner S D, Cully D F, Arena J P, Liberator P L, Rosenblum C I, Hamelin M, Hreniuk D L, Palyha O C, Anderson J, Paress P S, Diaz C, Chou M, Liu K K, McKee K-K, Pong S-S, Chaung L-Y, Elbrecht A, Dashkevicz M, Heavens R, Rigby M, Sirinathsinghji D, Dean D C, Melillo D G, Patchett A A, Nargund R, Griffin P R, DeMartino J A, Gupta S K, Schaeffer J A, Smith R G, Van der Ploeg L H T; A receptor in pituitary and hypothalamus that functions in growth hormone release. Science 273:974-977 (1996).

4. Li A, Cheng G, Zhu G H, Tarnawski A S; Ghrelin stimulates angiogenesis in human microvascular endothelial cells: Implications beyond GH release. Biochem. Byophis. Res. commun. 353:238-43 (2007).

5. Li W G, Gavrila D, Liu X, Wang L, Gunnlaugsson S, Stoll L L, McCormick M L, Sigmund C D, Tang C, Weintraub N L; Ghrelin inhibits proinflammatory response and nuclear factor-kappa B activation in human endothelial cells. Circulation 109:2221-6 (2004).

6. Dixit V D, Schaffer E M, Pyle R S, Collins G D, Sakthivel S K, Palaniappan R, Lillard J W Jr, Taub D D; Ghrelin inhibits leptin-and activation-induced proinflammatory cytokines expression by human monocytes and T cells. J. Clin. Inv. 114:57-66 (2004).

7. van der Lely A J, Tschop M, Heiman M L, Ghigo E; Biological, physiological, pathophysiological, and pharmacological aspects of ghrelin. Endocr Rev 25:426 457 (2004).

8. Baldanzi G, Filigheddu N, Cutrupi S, Catapano F, Bonissoni S, Fubini A, Malan D, Baj G, Granata R, Broglio F, Papotti M, Surico N, Bussolino F, Isgaard J, Deghenghi R, Sinigaglia F, Prat M, Muccioli G, Ghigo E, Graziani A; Ghrelin and des-acyl ghrelin inhibit cell death in cardiomyocytes and endothelial cells through ERK1/2 and PI 3-kinase/AKT. J Cell Biol. 159:1029-37 (2002).

9. Delhanty P J, van der Eerden B C, van der Velde M, Gauna C, Pols HA, Jahr H, Chiba H, van der Lely A J, van Leeuwen J; Ghrelin and unacylated ghrelin stimulate human osteoblast growth via mitogen-activated protein kinase (MAPK)/phosphoinositide 3-kinase (PI3K) pathways in the absence of GHS-R1a. J Endocrinol. 188:37-47 (2006).

10. Choi K, Roh S G, Hong Y H, Shrestha Y B, Hishikawa D, Chen C, Kojima M, Kangawa K, Sasaki S; The role of ghrelin and growth hormone secretagogues receptor on rat adipogenesis. Endocrinology. 144:754-9 (2003).

11. Sorrentino S A, Bahimann F H, Besler C, Muller M, Schulz S, Kirchhoff N, Doerries C, Horvath T, Limbourg A, Limbourg F, Fliser D, Haller H, Drexler H, Landmesser U; Oxidant stress impairs in vivo reendothelialization capacity of endothelial progenitor cells from patients with type 2 diabetes mellitus: restoration by the peroxisome proliferator-activated receptor-gamma agonist rosiglitazone. Circulation 116:163-73 (2007).

12. Brizzi M F, Dentelli P, Pavan M, Rosso A, Gambino R, Grazia De Cesaris M, Garbarino G, Camussi G, Pagano G, Pegoraro L; Diabetic LDL inhibits cell-cycle progression via STAT5B and p21 (waf). J Clin Invest. 109:111-9 (2002).

13. Thum T, Fraccarollo D, Schultheiss M, Froese S, Galuppo P, Widder J D, Tsikas D, Ertl G, Bauersachs J; Endothelial nitric oxide synthase uncoupling impairs endothelial progenitor cell mobilization and function in diabetes. Diabetes 56:666-74 (2007).

14. Dimmeler S, Zeiher A M; Vascular repair by circulating endothelial progenitor cells: the missing link in atherosclerosis? J Mol Med. 82:671-7 (2004).

15. Tepper O M, Galiano R D, Capla J M, Kalka C, Gagne P J, Jacobowitz G R, Levine J P, Gurtner G C; Human endothelial progenitor cells from type II diabetics exhibit impaired proliferation, adhesion, and incorporation into vascular structures. Circulation 106:2781-6 (2002).

16. Papayannopoulou T; Current mechanistic scenarios in hematopoietic stem/progenitor cell mobilization. Blood. 103: 1580-5 (2004).

17. Hattori K, Heissig B, Tashiro K, Honjo T, Tateno M, Shieh J H, Hackett N R, Quitoriano M S, Crystal R G, Rafii S, Moore M A; Plasma elevation of stromal cell-derived factor-1 induces mobilization of mature and immature hematopoietic progenitor and stem cells. Blood 97:3354-60 (2001).

18. Takahashi T, Kalka C, Masuda H, Chen D, Silver M, Kearney M, Magner M, Isner J M, Asahara T; Ischemia- and cytokine-induced mobilization of bone marrow-derived endothelial progenitor cells for neovascularization. Nat Med. 5:434-8 (1999).

19. Hill J M, Zalos G, Halcox J P, Schenke W H, Waclawiw M A, Quyyumi A A, Finkel T; Circulating endothelial progenitor cells, vascular function, and cardiovascular risk. N Engl J Med. 348:593-600 (2003).

20. Defilippi P, Rosso A, Dentelli P, Calvi C, Garbarino G, Tarone G, Pegoraro L, Brizzi; MFβ1 Integrin and IL-3R coordinately regulate STAT5 activation and anchorage-dependent proliferation. J. Cell Biol. 168:1099-1108 (2005).

21. Zhao W, Diz D I, Robbins M E; Oxidative damage pathways in relation to normal tissue injury. Br J Radiol. 80:S23-31 (2007).

22. Rosso A, Balsamo A, Gambino R, Dentelli P, Falcioni R, Cassader M, Pegoraro L, Pagano G, Brizzi M F; p53 Mediates the accelerated onset of senescence of endothelial progenitor cells in diabetes. J Biol Chem. 281 :4339-47 (2006).

23. Brummelkamp, T R., Bernards, R, and Agami, R; A system for stable expression of short interfering RNAs in mammalian cells. *Science* 296:550-553 (2002).

24. Dentelli P, Rosso A, Balsamo A, Colmenares Benedetto S, Zeoli A, Pegoraro M, Camussi G, Pegoraro L, Brizzi M F; C-KIT, by interacting with the membrane-bound ligand, recruits endothelial progenitor cells to inflamed endothelium. Blood. 109:4264-71 (2007).

25. Aranguren X L, Luttun A, Clavel C, et al.; In vitro and in vivo arterial differentiation of human multipotent adult progenitor cells. Blood. 109:2634-2642 (2007).

26. Cormier S, Vandormael-Pournin S, Babinet C, Cohen-Tannoudji M; Developmental expression of the Notch signaling pathway genes during mouse preimplantation development. Gene Expr. Patterns;4:713-717 (2004).

27. Hoff J; Methods of blood collection in the mouse. Lab. Animal. 29 (2000).

28. Zeoli A, Dentelli P, Rosso A, Togliatto G, Trombetta A, Damiano L, Francia di Celle P, Pegoraro L, Altruda F, Brizzi M F; Interleukin-3 (IL-3) promotes expansion of hemopoietic-derived CD45+ angiogenic cells and their arterial commitment via STAT5 activation. Blood in press.

29. Yamagishi S, Matsui T, Nakamura K; Kinetics, role and therapeutic implications of endogenous soluble form of receptor for advanced glycation end products (sRAGE) in diabetes. Curr Drug Targets. 8:1138-43(2007).

30. Dimri G P. What has senescence got to do with cancer? Cancer Cell. 7:505-12 (2005).

31. Vasa M, Fichtlscherer S, Aicher A, Adler K, Urbich C, Martin H, Zeiher A M, Dimmeler S. Number and migratory activity of circulating endothelial progenitor cells inversely correlate with risk factors for coronary artery disease. Circ Res. 89:E1-7 (2001).

32. Waltenberger J. Impaired collateral vessel development in diabetes: potential cellular mechanisms and therapeutic implications. Cardiovasc Res 49:554-60 (2001).

33. Abaci A, Oğuzhan A, Kahraman S, Eryol N K, Unal S, Arinç H, Ergin A. Effect of diabetes mellitus on formation of coronary collateral vessels. Circulation 99:2239-42 (1999).

34. Schalkwijk C G, Stehouwer C D. Vascular complications in diabetes mellitus: the role of endothelial dysfunction. Clin Sci (Lond) 109:143-59 (2005).

35. Kleinz M J, Maguire J J, Skepper J N, Davenport A P. Functional and immunocytochemical evidence for a role of ghrelin and des-octanoyl ghrelin in the regulation of vascular tome in man. Cardiovascular Research 69:227-235 (2006).

The invention claimed is:

1. A method for treatment of ischemia in a subject, comprising administering to the subject a therapeutically effective amount of (i) a polypeptide consisting of a fragment of unacylated ghrelin as set forth in SEQ ID NO: 1, said fragment being 5-18 amino acids in length and comprising amino acid residues 8 to 12 of SEQ ID NO: 1 and having a biological activity of SEQ ID NO: 1; or (ii) the polypeptide of (i) wherein said fragment has one or more conservative amino acid substitutions.

2. The method of claim 1, wherein the treatment increases neovascularisation at the site of ischemia.

3. The method of claim 1, wherein the treatment increases the number of circulating angiogenic cells (CAC) at the site of ischemia.

4. The method of claim 3, wherein the biological activity of SEQ ID NO: 1 includes reducing oxidative stress circulating angiogenic cells (CAC).

5. The method of claim 3, wherein the biological activity of SEQ ID NO: 1 includes reducing circulating angiogenic cells (CAC) senescence.

6. The method of claim 1, wherein the therapeutically effective amount varies from about 0.001 µg/kg to about 10 mg/kg.

7. The method of claim 1, wherein the subject suffers from type I or type II diabetes.

8. The method of claim 1, wherein the ischemia is associated with atherosclerotic vascular degeneration.

9. The method of claim 1, wherein the fragment comprises amino acid residues 6 to 13 of SEQ ID NO: 1.

10. The method of claim 1, wherein the polypeptide consists of an amino acid sequence selected from the group consisting of SEQ ID NO: 6, SEQ ID NO: 7 and SEQ ID NO: 8.

11. The method claim 1, wherein the polypeptide consists of amino acid sequence SEQ ID NO: 6.

12. The method of claim 9, wherein the polypeptide is in a cyclised form.

13. The method of claim 9, wherein the polypeptide comprises a linker moiety.

* * * * *

UNITED STATES PATENT AND TRADEMARK OFFICE
CERTIFICATE OF CORRECTION

PATENT NO.         : 8,476,408 B2
APPLICATION NO.    : 12/482882
DATED              : July 2, 2013
INVENTOR(S)        : Maria Felice Brizzi et al.

It is certified that error appears in the above-identified patent and that said Letters Patent is hereby corrected as shown below:

In the Claims:

In Column 29, Line 26, in Claim 4, delete "stress" and insert -- stress of --, therefor.

Signed and Sealed this
Tenth Day of September, 2013

Teresa Stanek Rea
*Acting Director of the United States Patent and Trademark Office*